US008032564B2

(12) United States Patent
Muret et al.

(10) Patent No.: US 8,032,564 B2
(45) **Date of Patent: *Oct. 4, 2011**

(54) SYSTEM AND METHOD FOR MONITORING AND ANALYZING INTERNET TRAFFIC

(75) Inventors: Paul N. Muret, Los Altos, CA (US); Hui Sok Moon, Campbell, CA (US)

(73) Assignee: Google Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/606,683

(22) Filed: Oct. 27, 2009

(65) Prior Publication Data

US 2010/0049847 A1 Feb. 25, 2010

Related U.S. Application Data

(63) Continuation of application No. 10/799,738, filed on Mar. 15, 2004, now Pat. No. 7,610,289, which is a continuation of application No. 09/679,297, filed on Oct. 4, 2000, now Pat. No. 6,792,458.

(60) Provisional application No. 60/157,649, filed on Oct. 4, 1999.

(51) Int. Cl.
*G06F 17/30* (2006.01)
*G06F 7/00* (2006.01)

(52) U.S. Cl. ........................................................ 707/803

(58) Field of Classification Search ................... 707/803
See application file for complete search history.

(56) References Cited

U.S. PATENT DOCUMENTS

| | | | | |
|---|---|---|---|---|
| 6,233,600 | B1 * | 5/2001 | Salas et al. | 709/201 |
| 6,360,246 | B1 * | 3/2002 | Begley et al. | 709/203 |
| 6,377,993 | B1 * | 4/2002 | Brandt et al. | 709/227 |
| 6,480,891 | B1 * | 11/2002 | Chernyak et al. | 709/223 |
| 6,691,259 | B1 * | 2/2004 | Mackey et al. | 714/46 |
| 6,701,323 | B2 * | 3/2004 | Sashino et al. | 707/103 R |
| 6,768,994 | B1 * | 7/2004 | Howard et al. | 707/10 |
| 6,789,115 | B1 * | 9/2004 | Singer et al. | 709/224 |
| 7,093,194 | B2 * | 8/2006 | Nelson | 715/513 |

* cited by examiner

*Primary Examiner* — Kuen S Lu
(74) *Attorney, Agent, or Firm* — Fish & Richardson P.C.

(57) ABSTRACT

A system and method for monitoring and analyzing Internet traffic is provided that is efficient, completely automated, and fast enough to handle the busiest websites on the Internet, processing data many times faster than existing systems. The system and method of the present invention processes data by reading log files produced by web servers, or by interfacing with the web server in real time, processing the data as it occurs. The system and method of the present invention can be applied to one website or thousands of websites, whether they reside on one server or multiple servers. The multi-site and sub-reporting capabilities of the system and method of the present invention makes it applicable to servers containing thousands of websites and entire on-line communities. In one embodiment, the system and method of the present invention includes e-commerce analysis and reporting functionality, in which data from standard traffic logs is received and merged with data from e-commerce systems. The system and method of the present invention can produce reports showing detailed "return on investment" information, including identifying which banner ads, referrals, domains, etc. are producing specific dollars.

12 Claims, 36 Drawing Sheets

Visitor Footprint

| Visitor Footprint: bmw2002.com | Entrance Time:<br>Exit Time: | | 2100 |
|---|---|---|---|

Visitor Footprint

IP Address    132.129.18.9
User Name    Jimbob
Pageviews    200
Hits    235,797
Bytes    925.9
Length of Visit    263 sec

2110 →

[Windows 2000]  2180  [N]  2120

Platform    Windows 2000
Browser    Netscape 4.7

2180

Referral

Referral    aol.com/dirsearch.adp
Keyword    Casting
Search Engine    google.com Domain    aol.com
Country    uk (United Kingdom)

2130 →  2140

Visitor Path 1. index.html (Entrance)
2. products/index.html
3. products/coolshoes.html
4. products/verycoolshoes.html
5. products/reallycoolshoes.html
6. help/reallycoolshoes.html
7. about/reallycoolshoes.html
8. help/reallycoolshoes.html
9. contact/helpform.html
10. contact/helpform.html (Exit)

2150 →

E-Commerce

Total Dollars    $200
Time of Purchase    May 12, 1999 12:14:22

Region    San Diego, CA (US)
Invoice ID    13344

2160 →

Streaming

Clip
1. thankyou.rm
2. welcome.asf

Media Player (Type)
RealPlayer 4.0 (rm)
Media Player 4.0 (asf)

Time (Resends, Failed)
300 sec (5,2)
200 sec (9,3)

Bytes Sent (Total)
2 MB (20 MB)
2.5 MB (3 MB)

2170 →

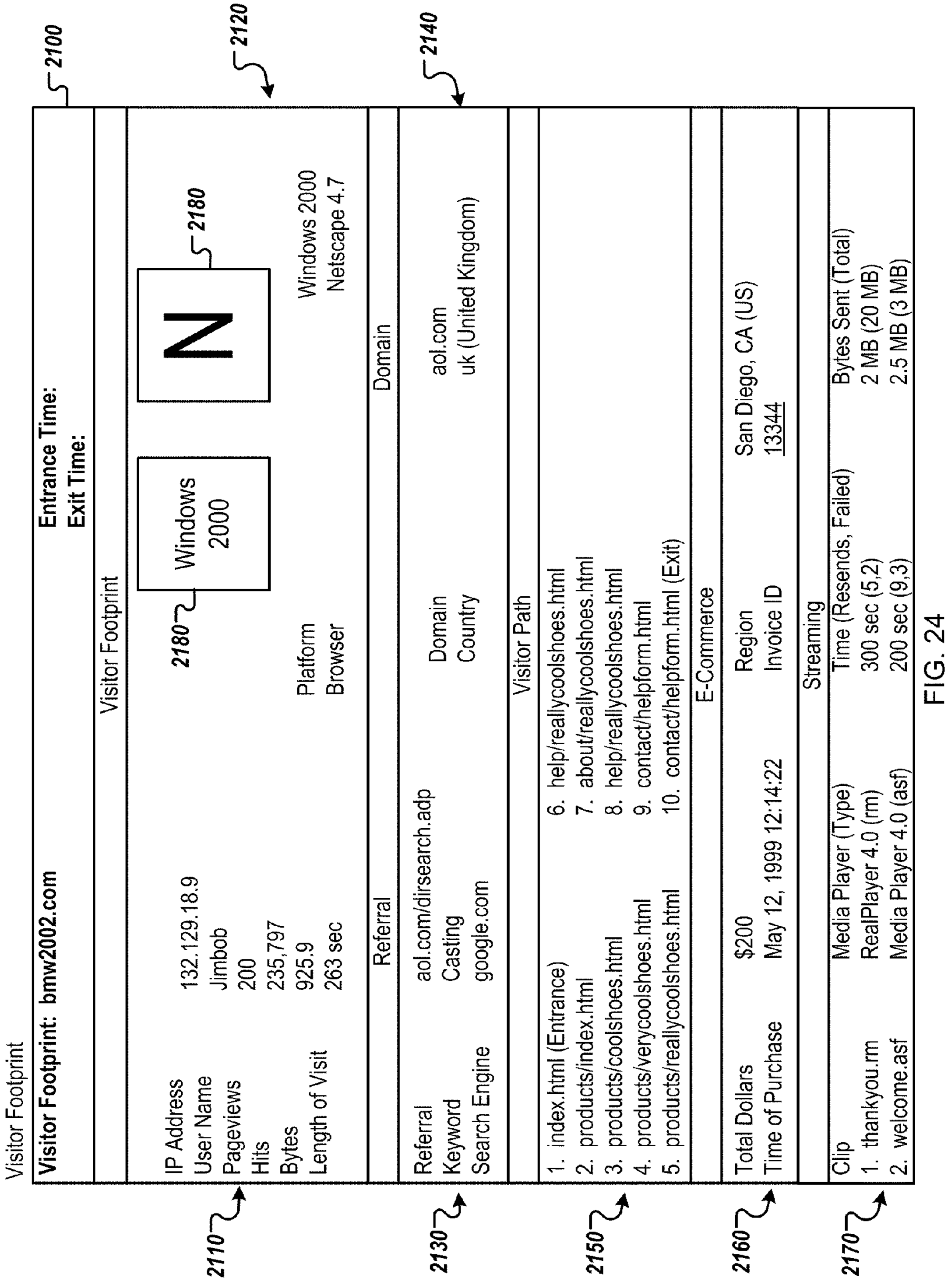

FIG. 24

SYSTEM AND METHOD FOR MONITORING AND ANALYZING INTERNET TRAFFIC

CROSS-REFERENCE TO RELATED APPLICATIONS

This application is a continuation application of and claims priority to U.S. application Ser. No. 10/799,738, filed on Mar. 15, 2004 entitled, "System and Method for Monitoring and Analyzing Internet Traffic," which issued as U.S. Pat. No. 7,610,289 on Oct. 27, 2009, which is continuation of U.S. application Ser. No. 09/679,297, filed Oct. 4, 2000, which issued as U.S. Pat. No. 6,792,458 on Sep. 14, 2004, which claims the benefit of U.S. Provisional Patent Application No. 60/157,649, filed Oct. 4, 1999. The disclosures of U.S. application Ser. Nos. 10/799,738, 09/679,297, and 60/157,649 are incorporated herein by reference in their entirety.

BACKGROUND OF THE INVENTION

1. Field of the Invention

The present invention relates to Internet traffic and, more specifically, to a system and method for monitoring and analyzing Internet traffic.

2. Description of Related Art

Internet web servers such as those used by Internet Service Providers (ISP), are typically configured to keep a log of server usage by the on-line community. For example, as a visitor to a website clicks on various hyperlinks and travels through a website, each step is recorded by the web server in a log. Each web page, image and multimedia file viewed by the visitor, as well as each form submitted, may be recorded in the log.

The type of information logged generally includes the Internet Protocol (IP) address or host name of the visitor, the time of the transaction, the request, the referring page, the web browser and type of platform used by the visitor, and how much data was transferred. When properly analyzed, this information can help marketing executives, webmasters, system administrators, business owners, or others make critical marketing, business, commerce and technical decisions. The data can be mined for all types of decision supporting information, e.g. analyzing which webbrowsers people are using, determining which banner ads are producing the most traffic, etc.

A problem with mining the raw log data for useful information is the shear volume of data that is logged each day. ISPs may have dozens of web servers containing thousands of websites that produce gigabytes of data each day. Providing a robust system that can be used on various platforms, that can efficiently process the huge amounts of data that are logged, and that can produce easy to use reports for each website in an automated fashion is a daunting task.

BRIEF SUMMARY OF THE INVENTION

In view of the above problems in the art, the present invention provides a system and method for monitoring and analyzing Internet traffic that is efficient, completely automated, and fast enough to handle the busiest websites on the Internet, processing data many times faster than existing systems.

The system and method of the present invention processes data by reading log files produced by web servers, or by interfacing with the web server in real time, processing the data as it occurs. The system and method of the present invention can be applied to one website or thousands of websites, whether they reside on one server or multiple servers.

The multi-site and sub-reporting capabilities of the system and method of the present invention makes it applicable to servers containing thousands of websites and entire on-line communities.

The system and method of the present invention can create reports for individual websites, as well as reports for all of the websites residing on a single server or multiple server. The system can also create reports from a centralized system, in which reports are delivered upon request directly from the system database via a Common Gateway Interface (CGI).

The system and method of the present invention can also include real-time analysis and reporting functionality in which data from web servers is processed as it occurs. The system and method of the present invention can produce animated reports showing current activity on the web server, which can be used by administrators and managers to monitor website effectiveness and performance.

The system and method of the present invention can further include e-commerce analysis and reporting functionality in which data from standard traffic logs is received and merged with data from e-commerce systems. The system and method of the present invention can produce reports showing detailed "return on investment" information, including identifying which banner ads, referrals, domains, etc. are producing specific dollars.

The present invention can be achieved in whole or in part by a system for analyzing and monitoring internet traffic, comprising a relational database, a log engine that processes log files received from at least one internet server and stores data processed from the log files in the relational database; and a report engine that generates reports based on the processed data stored in the relational database. The system and method of the present invention preferably utilizes Visitor Centric Data Modeling, which keeps data associated with the visitor that generated it, and that allows for the cross-comparing of different elements of data coming from different log entries or different log files altogether.

The accompanying drawings, which are incorporated in and constitute a part of this specification, illustrates embodiments of the invention and, together with the description, serve to explain the principles of the invention.

BRIEF DESCRIPTION OF THE DRAWINGS

FIG. 24 is an example of a visitor footprint report created by the system of the present invention;

DETAILED DESCRIPTION OF THE INVENTION

Figure 1:
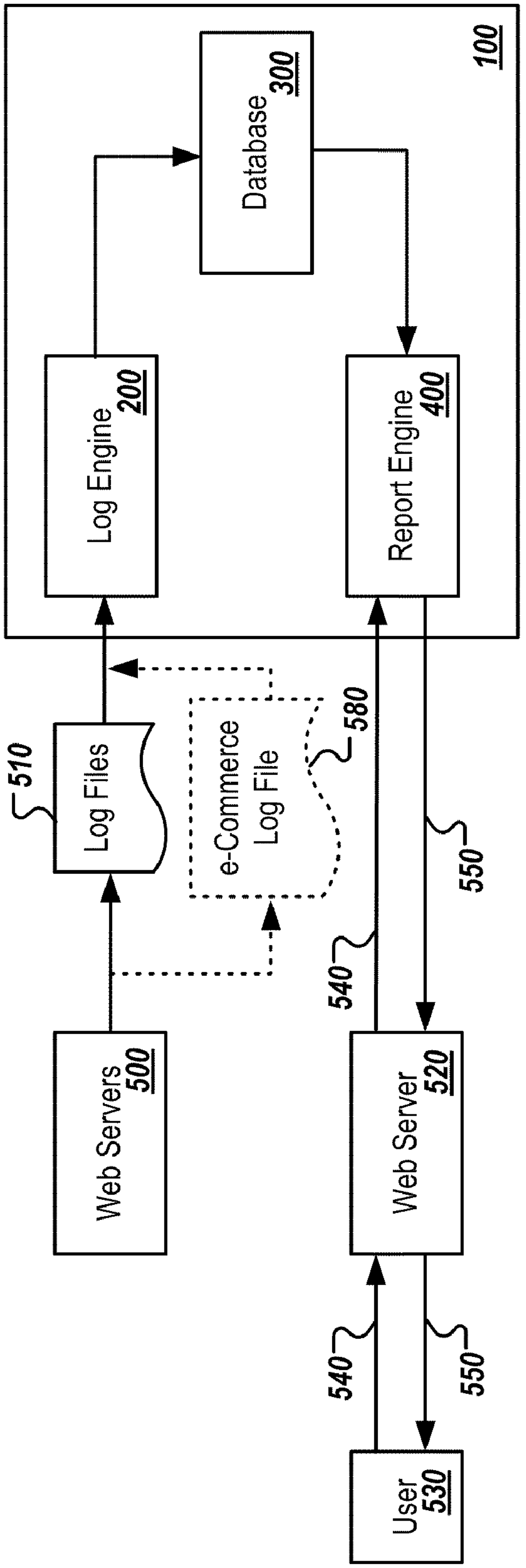
FIG. 1 is a schematic diagram of a system for monitoring and analyzing Internet traffic, in accordance with the present invention.

FIG. 1 illustrates a system 100 for monitoring and analyzing Internet traffic, in accordance with the present invention. The system 100 comprises a log engine 200, a database 300 and a report engine 400.

In operation, log files 510 generated by web servers 500 are sent to the log engine 200. Web (Internet) traffic is served by the web server 500. The web server 500 can host one or many individual websites. As visitors access the web servers 500 for content, each website hit or transaction is appended to a log. Each web server will typically have its own log file. Multiple websites on a single server could be logged centrally in one log file, or could be configured so that each website has its own log file. The system 100 is able to handle all of these different architectures.

The entries on each of the log files 510 are interleaved so that individual website hits or transactions are recorded in the order they are received. If a single log file contains log entries from multiple websites, the log entries are also interleaved so that individual hits or transactions from each website are recorded in the order they are received. Each line in the log files 510 represents a hit or a transaction from the website on one of the web servers 500.

In addition to normal web traffic, many websites contain e-commerce enabled virtual "shopping carts" that allow visitors to securely buy products directly from the website. The system 100 can optionally analyze the demographics of online shopping by receiving e-commerce log files 580 produced by e-commerce enabled websites. The e-commerce log files 580 are transaction logs that contain information about each order placed on the website. Each of the e-commerce log files 580 generally contains data on the pricing of products purchased, dollar amounts and shipping regions. Sensitive information such as credit numbers, individual names and e-mail addresses are generally not stored on the e-commerce log files 580. Dashed lines are used to represent the e-commerce log files 580 to indicate that the e-commerce functionality is an optional feature of the system 100.

The preferred embodiment of the log engine 200 is responsible for processing all of the log files 510 and 580, domain name system (DNS) resolving and updating the database 300. The log engine 200 utilizes memory buffers, fixed-width data models and other techniques to efficiently process the log files 510 and 580. In addition, the log engine 200 can be optionally configured to access live data. The operation of the log engine 200 will be described in more detail below.

The log engine 200 efficiently reads each line in each of the log files 510 and separates each line into its individual parts. The individual parts can include fields such as the IP address, time stamp, bites sent, status code, referral, etc. The log engine 200 utilizes a technique called Visitor Centric Data Modeling. Rather than parsing each log line and counting how many of one type of browser was used or how many times a particular webpage was viewed, Visitor Centric Data Modeling keeps that data associated with the visitor that generated it. One of the primary advantages of Visitor Centric Data Modeling is the ability to cross compare different elements of data coming from different log entries or different log files altogether. Visitor Centric Data Modeling allows one to determine what percentage of users that originated from a Yahoo™ search looked at a particular webpage.

A second benefit of Visitor Centric Data Modeling is reduction of overall data processing. Because many elements of the data will be the same during a visitor's visit, the information only needs to be processed once per visitor, rather than once per log line. For example, the primary domain name of the visitor will be the same for each log entry produced by a particular visitor. Visitor Centric Modeling allows one to process this information only once per visitor. Additional details on how the log engine 200 utilizes the Visitor Centric Data Modeling will be provided below.

Figure 2:
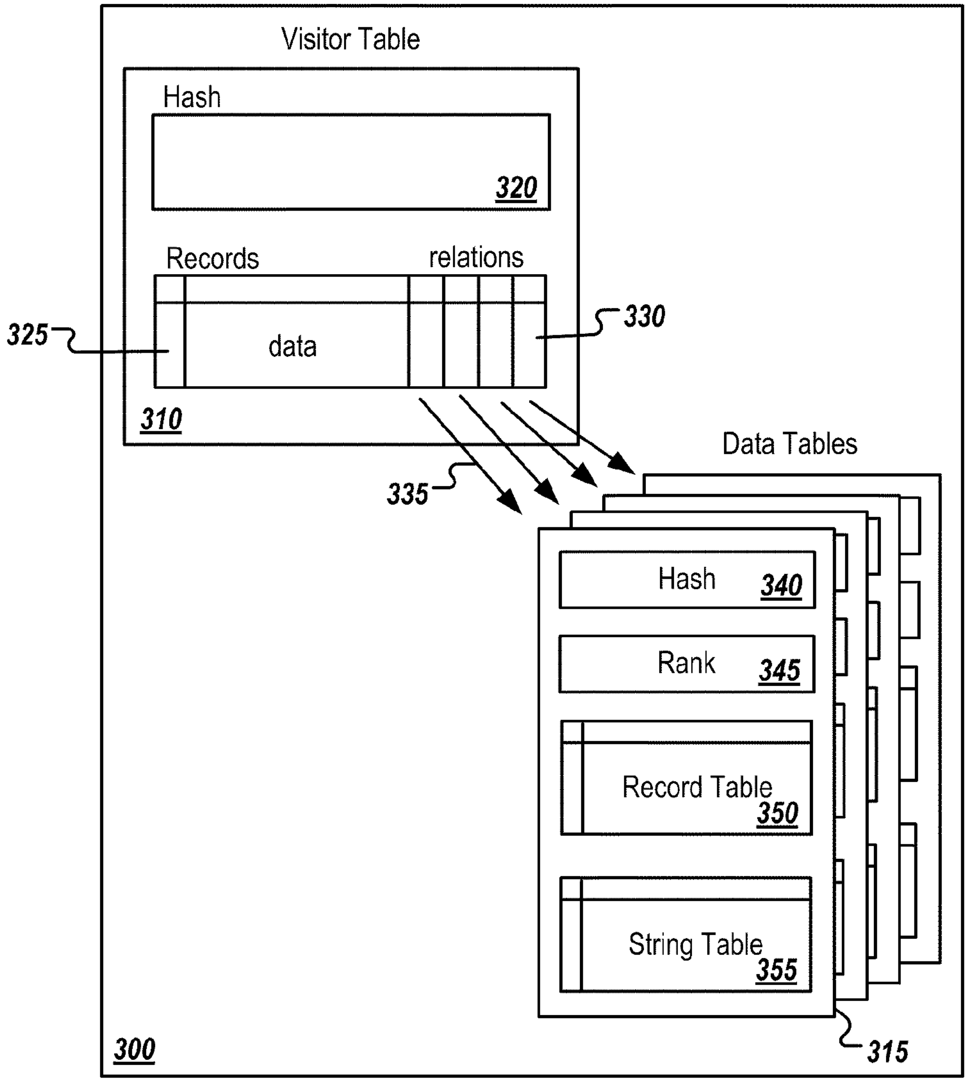
FIG. 2 is a schematic diagram of a series of hash tables stored by the database shown in FIG. 1.

The log engine 200 processes each log entry and updates the database 300. The database 300 contains a series of hash tables. The database 300 comprises a series of hash tables, as shown in FIG. 2. The hash tables comprise a visitor table 310 and associated data tables 315.

The visitor table 310 contains the central record for each visitor to a website. The hits, bytes, page views, and other fixed data parameters (hereinafter collectively referred to as "traffic information") are stored directly in the visitor table 310. The remaining non-unique parameters, e.g., domain names, types of web browsers, referring web sites, etc., are stored relationally in respective data tables 315. For example, one of the data tables 315 could be configured to store a list of the different domain names from which the visitors to the website being monitored by the system 100 originate, while another of the data tables 315 could be configured to store the names of the different types of web browsers used by the visitors to the web site being monitored by the system 100.

The database 300 is relational and centers the data in the visitor table 310, creating a Visitor Centric Data Model. The visitor table 310 contains a hash table 320 that is used for quickly seeking visitor records. Below the hash table 310, the actual records 325 contain the traffic information of each visitor. Each unique visitor will have their own record in the visitor table 310.

The visitor table 310 is relational in nature and has a relations area 330 that contains pointers 335 to records 350 within the data tables 315. As discussed above, each of these data tables 315 store different visitor parameters such as domain, browser, and referral. Besides vastly reducing the storage requirements relative to a non-relational database, the data tables 315 can be used to create statistical reports on the usage of different visitor parameters.

Each data table 315 contains a hash table 340, a rank table 345, a record table 350, and a string table 355. The hash table 340 is used to seek records in the record table 350. The rank table 345 is used to keep track of the top entries in the record table 350 based on the number of pointers 335 set to the records in the record table 350. This is useful for quick access to reports. The record table 350 stores the actual records within the data table 315 including the traffic information associated with the parameter associated with the data table 315. The record table 350 does not store the value of the parameter. Instead, the record table 350 contains a pointer to a record in the string table 355. Each of these subtables (320, 325, 340, 345, 350, 355) has fixed width records allowing for efficient reading, writing, and copying of the entire data sets.

The relational structure of the database 300 has at least two advantages. First, the visitor table 310 simplifies the task of processing each hit because, once the visitor is identified, the appropriate visitor table 310 can be identified and updated accordingly. Second, the data tables 315 simplify the task of report generation, because each of the data tables 315 stores a specific parameter (e.g., the names of the web browsers used by the visitors) and are ranked. Thus, each of the data tables 315 can easily deliver the top list of entries for a particular report.

Referring back to FIG. 1, once the log files 510, and optionally the e-commerce log files 580, are processed by the log engine 200, and the database 300 is updated, the system 100 is ready to deliver reports based on the updated information in the database 300. A user 530 sends a report request 540 to the report engine 400 via a web server 520. The report engine 400 obtains the data required to generate the report from the database 300, generates the report, and delivers the generated report 550 to the user 530 via the web server 520.

The web server 520 can optionally be one of the web servers 500 that created the log files 510 and 580. The report engine 400 preferably utilizes javascript application techniques, dictionaries, and templates to provide flexible, efficient, customizable and attractive reports, as will be explained in more detail below. Reports are generated on the fly when requested by the user 530 using the standard Common Gateway Interface (CGI) of the web server 520. Storage requirements are kept small as all HTML and graphics for the reports are generated as needed.

Log Engine (200)

Figure 3:
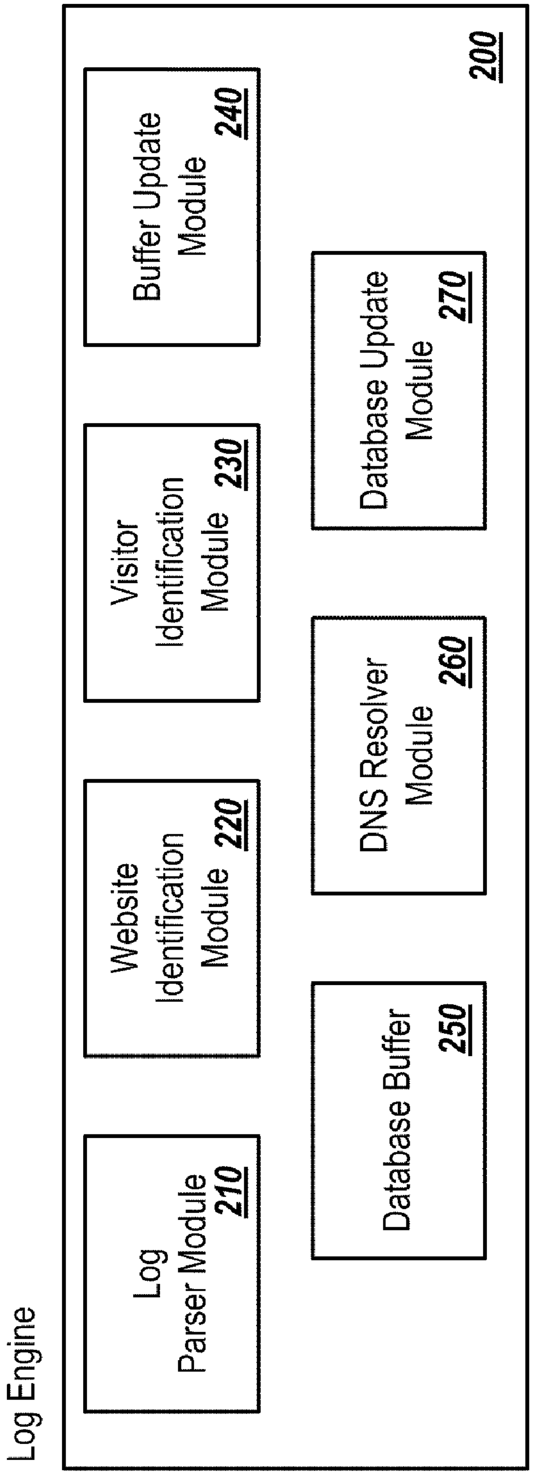
FIG. 3 is a block diagram of a preferred embodiment of the log engine shown in FIG. 1.

FIG. 3 is a block diagram of a preferred embodiment of the log engine 200. The log engine preferably comprises a log parser module 210, a website identification module 220, a visitor identification module 230, a buffer update module 240, a DNS resolver module 250, a database buffer 260 and a database update module 270.

The log parser module 210 is responsible for the actual reading and processing of the log files 510 and the e-commerce log files 580. The log parser module 210 can be configured to process either static log files or log files that are being generated live in real-time. The log parser module 210 loads each log line from the log files 510 and 580 and separates each log line into its individual fields.

The website identification module 220 is primarily used when multiple websites are being logged to the same file. A class of web hosting known as "virtual hosting" or "shared hosting" allows ISPs to offer solid performing website hosting service at reasonable prices. By setting up a robust set of servers with virtual hosting capable software, ISPs can place multiple websites on the servers, thus allowing the website owners to share the cost of the servers, maintenance, and networking.

However, as ISPs squeeze more and more websites onto a server in order to generate profit in an ever increasingly competitive industry, creating a system that is scalable becomes more and more difficult. One problem that administrators soon face is the number log files open during operation. Typically they will have at least one log file 510 for each website. As they add hundreds or thousands of websites to a server, the handling of all log files 510 becomes difficult. Moving, rotating and archiving all of the individual log files 510 becomes a burden. Also, system performance is compromised as resources are allocated to each open log file (many systems have a hard limit to the number of files that can be open simultaneously).

To solve this problem, the system and method of the present invention utilizes Subreport/Multisite Reporting Technology. This technology allows hosting providers to centralize the logging for all websites. Each server can have just one log file 510 for all websites, keeping resources in check. There is just one log file 510 to manage, rotate, process and archive, thus making the administrator's duties easier, less expensive and more scalable.

This website identification module 220 identifies each hit as belonging to a particular website. If the log file 510 or e-commerce log file 580 has data from only one website, then the task is simple and is handled through straight configuration. However, if the log file 510 or e-commerce log file 580 contains data from multiple websites, then the website identification module 220 employs a series of regular expression filters to perform the website identification. The website identification module 220 must be flexible and be able to pull any consistent part of the log file 510 for website identification. The website identification performed by the website identification module is later used to determine what portion of the database 300 to write the data to.

As discussed above, the log engine 200 utilizes Visitor Centric Data Modeling. The first step in using a Visitor Centric Data Model is to be able to identify the specific visitor within each log file line. The visitor identification module 230 analyzes the fields in each hit (log file line) and identifies the hit as belonging to a new or existing visitor. Based on a unique identifier, such as an IP number or session id and a timestamp, the visitor identification module 230 determines which visitor record in the database 300 will need to be updated. If the timestamp of the hit is within a predetermined amount of time (e.g., 30 minutes) of an existing visitor, then the hit is considered as coming from that visitor.

The buffer update module 240 updates the parameters of the visitor record found by the visitor identification module 230 and stored on the database buffer 250 with the current hit's information. The timestamp of the hit is used to keep the chronological order of events intact.

The database buffer 250 is a volatile storage area, preferably RAM memory, that mirrors the actual database 300. At the beginning of processing, current data is read from the database 300 into the database buffer 250. After processing is complete, data is written back to the database 300. The purpose of the database buffer 250 is to speed up the processing of each hit. Instead of accessing the actual database 300 for each hit in the log file 510 or e-commerce log file 580, the database buffer 250 allows the log engine 200 to build up the data in the faster RAM memory location of the database buffer 250 and then flush data to the database 300 in larger chunks. The operation of the database buffer 250 will be explained in more detail below.

Before outputting the data to the database 300, the data is passed through the DNS resolver module 260 for reverse DNS resolution of IP addresses. Most web servers log only the IP address of the visitor and not the host and domain information. The domain information provides valuable data about the physical and network location of visitors. The DNS resolver module 260 employs a customized resolution routine designed specifically to speed up the process of typically slow DNS operations.

The database update module 270 performs the task of updating the database with the contents of the database buffer 260. The database update module 270 performs some processing (e.g., visitor sorting) before writing to the database 300.

Preferred control routines for the log parser module 210, website identification module 220, visitor identification module 230, buffer update module 240, DNS resolver module 260 and database update module 270 will be described below.

Log Parser Module (210)

Figure 4:
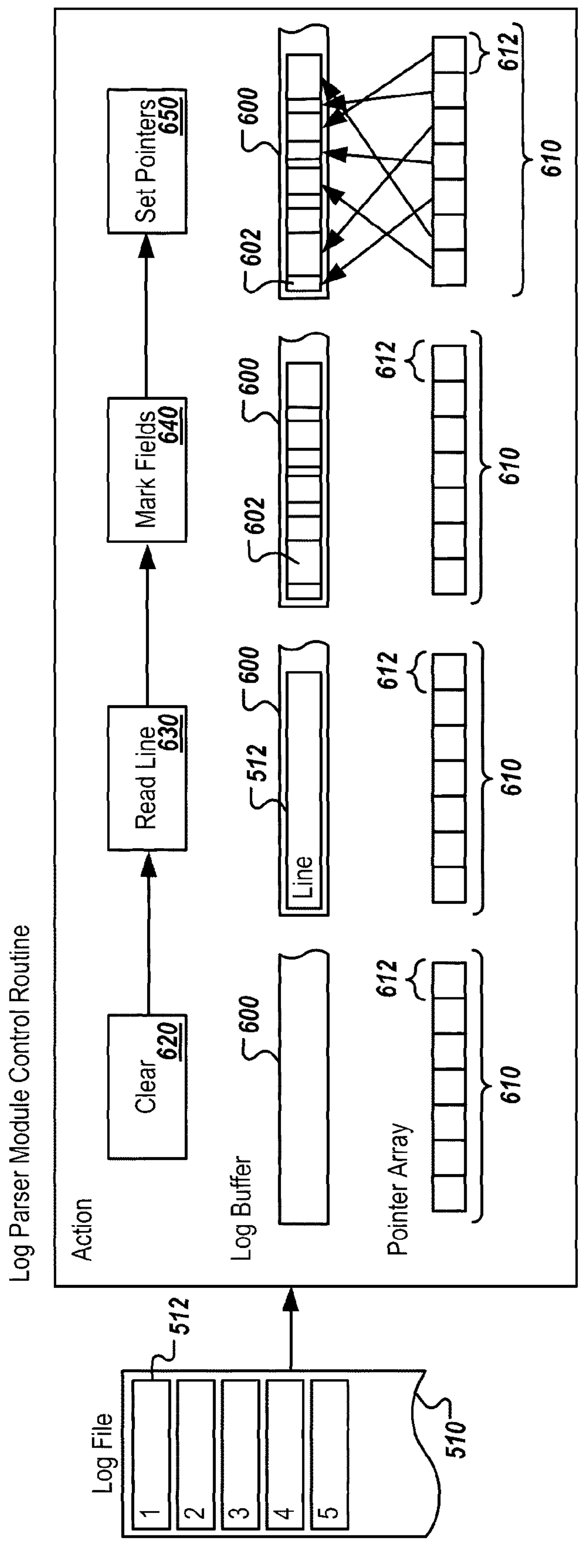
FIG. 4 is a flowchart and schematic diagram illustrating a preferred control routine for the log parser module of FIG. 3.

FIG. 4 is a flowchart and schematic diagram illustrating a preferred control routine for the log parser module 210 of FIG. 3, configured to process static log files 510. One of the most time consuming operations is reading and processing the raw log files 510. With individual log files 510 containing potentially over a gigabyte of data, getting the raw data into the system 100 is an important step.

The purpose of the log parser module 210 is to efficiently read each log line 512 and separate it into its individual fields. The fields can include the IP address, timestamp, bytes sent, status code, referral, etc. As discussed above, each log line 512 in the log file 510 represents a hit or transaction from one of the web servers 500.

The log parser module 210 employs a log buffer 600 and a pointer array 610 that is reused for each log line 512 in the log file 510. Thus, memory allocation for this log parser module 210 is only done at startup. The states of the log buffer 600 and pointer array 610 at each step in the control routine shown in FIG. 4 are represented schematically under the corresponding step in the control routine.

The control routine starts at step 620, where the pre-allocated log buffer 600 and the pointer array 610 are cleared. The log buffer 600 is cleared by setting the first character in the log buffer 600 to zero. The pointer array 610 is cleared by setting the values of all the individual pointers 612 to zero. It is important for stable processing to set all of the pointers in the pointer array 610 to zero before using the pointer array 610.

The control routine then continues to step 630, where the next log line 512 in the log file 510 is read into the log buffer 600. For a log parser module 210 that is configured to process static log files 510, step 630 is accomplished using standard file access library calls.

The control routine then proceeds to step 640, field spacers are identified in the log buffer 600 and marked. The field spacers could be spaces, tabs, commas, or anything that can be used as the separator between the fields in the logging format.

At step 650, the marked field spacers are replaced with a zero and the appropriate pointer 612 is set to the next character in the log buffer 600. Although steps 640 and 650 are shown as separate steps for purposes of illustration, they are preferably performed at substantially the same time. Thus, with a single loop and without moving, copying or allocating any memory, the log buffer 600 containing the single log line 512 is converted into a series of smaller character strings, each representing a particular field 602, and with each zero terminated.

The pointers 612 in the pointer array 610 can then be used to access the fields 602 as if they were separate strings. Accordingly, with minimal processing and absolutely no iterative memory allocation, each log line 512 is read and efficiently separated into its fields 602.

Real-Time Control Routine for Log Parser Module (210)

Figure 5:
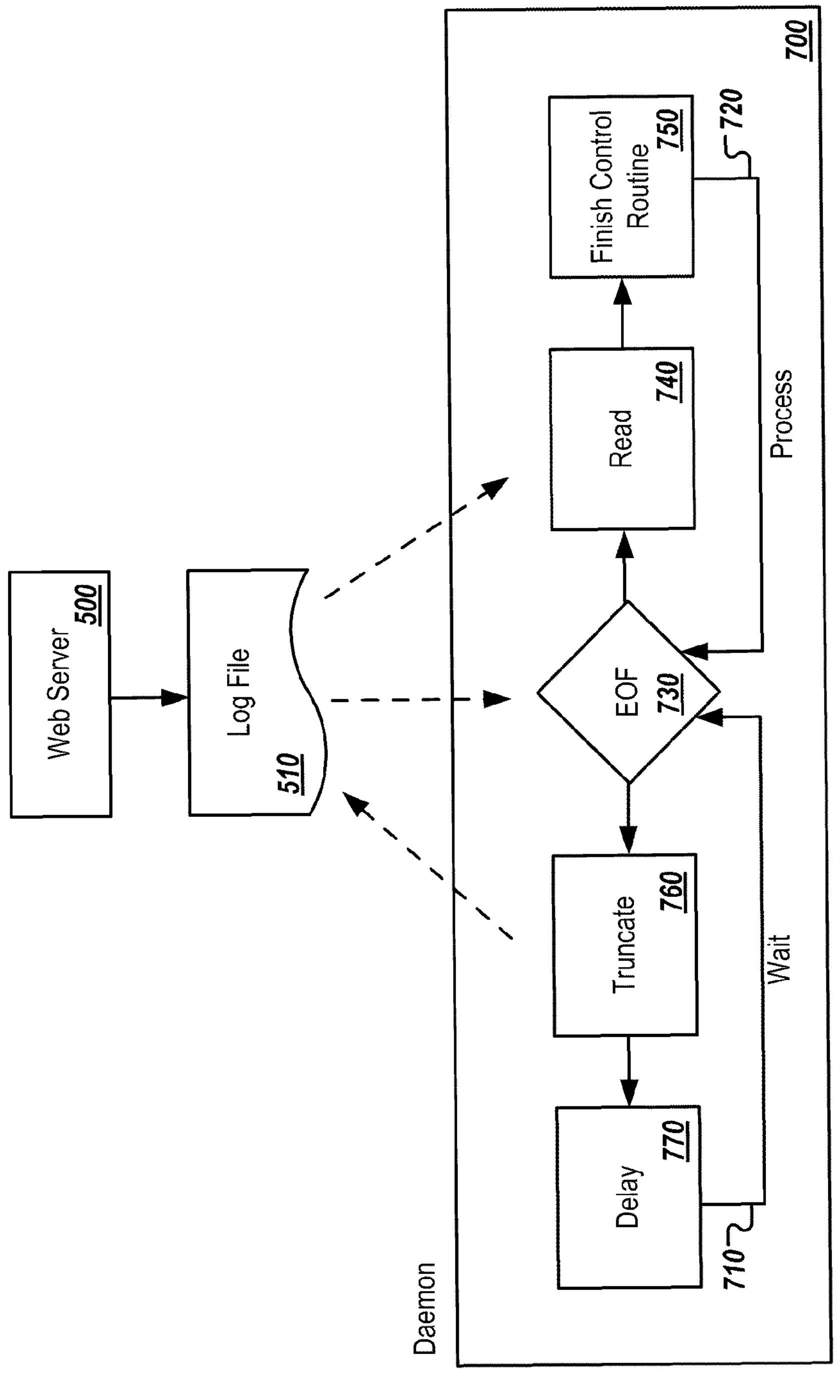
FIG. 5 is a flowchart and schematic diagram of a preferred control routine for the read line step of FIG. 4, for accessing and processing log file data in real time.

FIG. 5 is a flowchart and schematic diagram of a preferred control routine for the read line step of FIG. 4, for accessing and processing log file data in real time. A web server 500 under normal configuration is shown. The web server 500 handles all requests as they come in and logs each hit to the log file 510 by appending the log file 510 with data from each request.

The built in log file 510 acts as a buffer. It is the simplest and most robust way to pass data between the web server 500 and the live data access routine 700. The live data access routine 700 can be turned on or off at will. Once started, the live data access routine 700 runs as a low priority daemon. The live data access routine 700 can exist in two states: wait 710 and process 720, toggling between the two as data arrives into the buffer 510.

As long as more data exists in the log file 510, the system will stay in the process loop 720. The control routine starts at step 730, where the system checks for an "End of File" mark in the log file 510. As long as this mark is not detected, control moves to read step 740, where the next line in the log file 510 is read into the system. Control then continues to the finish control routine step 750, which finishes the control routine steps in the log parser control routine of FIG. 4, starting with the mark fields step 640 in FIG. 4. All of the read, write and EOF routines are autonomous, which means the web server 500 can continue to write new data to the end of the log 510 during the live data access routine 700.

Once the live data access routine 700 catches up and finishes the log file 510 by reaching the "End of File" marker, control moves to truncate step 760, where the log file 510 is immediately truncated. The truncation call sets the size of the log file 510 to zero. Since appended files always check file sizes before writing, the next write from the web server 500 will automatically start at the beginning of the log file 510.

Control them moves to delay step 770, which delays the control routine for a configurable amount of time (typically <=1 second). After this delay interval, control returns to the EOF step 730, where the existence of new data is checked.

As long the log file 510 is empty, the live data access routine 700 will remain in the wait loop 710. In this manner, the live data access routine 700 has real-time access to write data, while maintaining an arms length from the web server 500 itself.

Website Identification Module (220)

Figure 6:
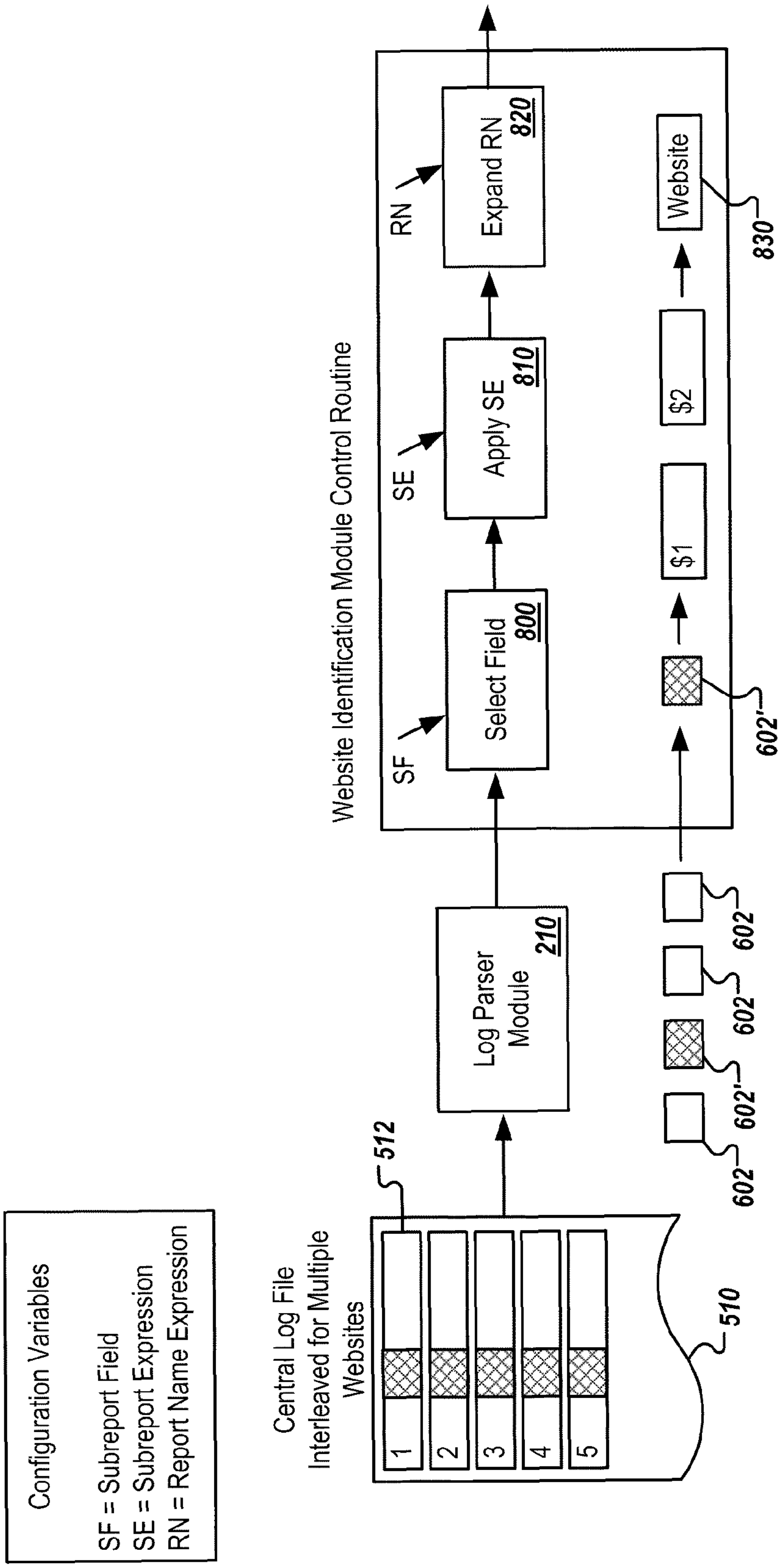
FIG. 6 is a flowchart and schematic diagram illustrating a preferred control routine for the website identification module of FIG. 3.

FIG. 6 is a flowchart and schematic diagram illustrating a preferred control routine for the website identification module 220 of FIG. 3, which is designed to identify the website that created each log line 512 in a log file 510. The log lines 512 are interleaved and written to the log file 510 as hits occur. The format of the log file 510 may vary from provider to provider. Some may use the canonical domain name in the log file 510, while others will use a subdirectory in the URI to identify the website.

There are three configuration variables that pertain to the control routine shown in FIG. 6. The subreport field (SF) specifies which field in the log file 510 contains the website identifier text. The subreport expression (SE) is a POSIX extended regular expression that is used to capture all or part of the field specified by SF. The report name expression (RN) is used to build the website name from the information captured by SE.

As discussed above, the log parser module 210 processes each log line 512 one at a time, and separates the log line 512 into separate fields 602. In the log file 510 shown in FIG. 6, log line field 602' contains the website identifier text, and is also indicated in FIG. 6 with shading.

The control routine for the website identification module begins at step 800, where log line field 602' is selected using the SF configuration variable. The control routine then continues to step 810, where the subreport expression (SE) is applied to the log line field 602' selected at step 800. This is done using POSIX extended regular expressions. The operator of the system 100 will need to be familiar with regular expressions or seek assistance from the manuals or technical support. The SE expression is used to match part or all of log line field 602'. Parenthesis are used to define what is to be matched. For example, to simply capture the entire field, the SE expression "(.*)" would be used. Whereas, to capture the last parts of a "www" domain name, the expression "www\.(.*)" could be used. Whatever is matched inside the parenthesis is placed into a first variable $1. If there are multiple sets of parenthesis, then subsequent matched components are placed into additional variables (e.g., $2, etc.). In the example shown in FIG. 6, two variables, $1 and $2, are used.

Next, at step 820, the $1 and $2 variables are used to generate the name 830 of the website. Using the report name expression (RN), the variables $1 and $2 are replaced with the actual contents of the matched components. For example, if the following configuration parameters are set:

SF=2

SE=SITE:(.*)

RN=www.mydomain.com/$1 and the following space-separated log line was processed:

123.12.3.1 2000-08-02 SITE:human-resources /index.html 200 1234 the website identification module 220, at step 800, would select "SITE:human-resources" as log line field 602' in the log line 512. The SE would capture everything after the "SITE:" part of log line field 602' as defined by the parenthesis location in the SE expression. This information is placed into the $1 variable. The website name 830 is then identified at step 820 by expanding the RN expression and replacing the $1 variable with the actual contents of the match. In this example, the resulting website name 830 is "www.mydomain.com/human-resources".

Visitor Identification Module (230)

Figure 7:
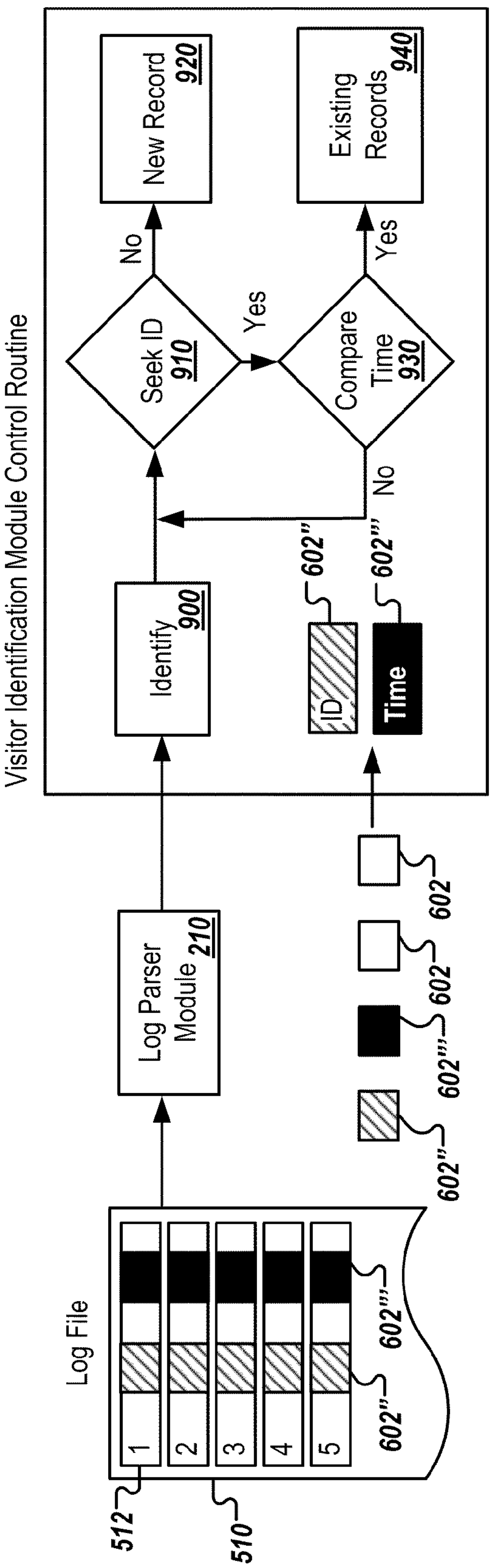
FIG. 7 is a flowchart and schematic diagram illustrating a preferred control routine for the visitor identification module of FIG. 3.

FIG. 7 is a flowchart and schematic diagram illustrating a preferred control routine for the visitor identification module 230 of FIG. 3. The log file 510 contains a number of log lines 512 or hits. Because the log lines 512 are interleaved, each log line 512 can be from a different visitor. As discussed above, the log parser module 210 processes each log line 512 in the log file 510, and places the information in the log buffer. The log line fields 602 are separated and the data is passed to the visitor identification module 230.

In the log file 510 shown in FIG. 7, log line field 602" contains the ID value and log line field 602'" contains the timestamp of the hit. Log line fields 602" and 602'" are also indicated in FIG. 7 with shading.

The control routine for the visitor identification module 230 begins at step 900, where log line fields 602" and 602'" are selected, as represented schematically under the Identify step 900 in FIG. 7. The control routine then continues to step 910, where the control routine looks up the ID value 602" in the visitor hash table 320 of the visitor table 310 (shown in FIG. 2). If the ID value 602" does not exist in the visitor hash table 320, control continues to step 920, where a new visitor record is created in the visitor hash table 320. If the ID value 602" does exist in the visitor hash table, control skips to step 930.

At step 930, the timestamp 602'" of the log line 512 is checked against the time range of the visitor record in the visitor hash table that corresponds to the ID value 602". If the timestamp 602'" falls within a predetermined allowable range, control continues to step 940, where the visitor record identified by the ID value 602" in the visitor hash table is determined to be the existing visitor. Otherwise, control jumps back to step 910, where the seek continues through records not previously searched until either a new record is created or another existing visitor is found.

The Visitor Centric Data Modeling described above has a very important and powerful benefit for real world applications. Many systems or websites will use multiple servers either mirroring each other or each handling a different part of a website. Extremely busy websites will often use an array of servers to handle the extreme load of traffic. Other websites may have a secure server area that resides on a special machine.

Whether for robustness or functionality, multiple server architecture is a common practice and appears to create a unique problem for internet traffic analysis and reporting. Each web server 500 will create its own log file 510, recording entries from visitors as they travel through the website. Often, a single visitor will create log entries in the log file 510 for each web server 500, especially if the web servers 500 perform different functions of the website.

It is desirable to be able to merge and correlate more than one log file 510 so as to have a complete and single record of a particular visitor. The Visitor Centric Data Modeling described above makes this ability automatic. Since each hit is uniquely identified to a particular visitor and the timestamp of the hit is recorded, determining the order and location of the hits do not require any additional engineering. The system and method of the present invention will automatically correlate the multiple log files as if they were coming from a single log file.

Buffer Update Module (240)

Figure 8:
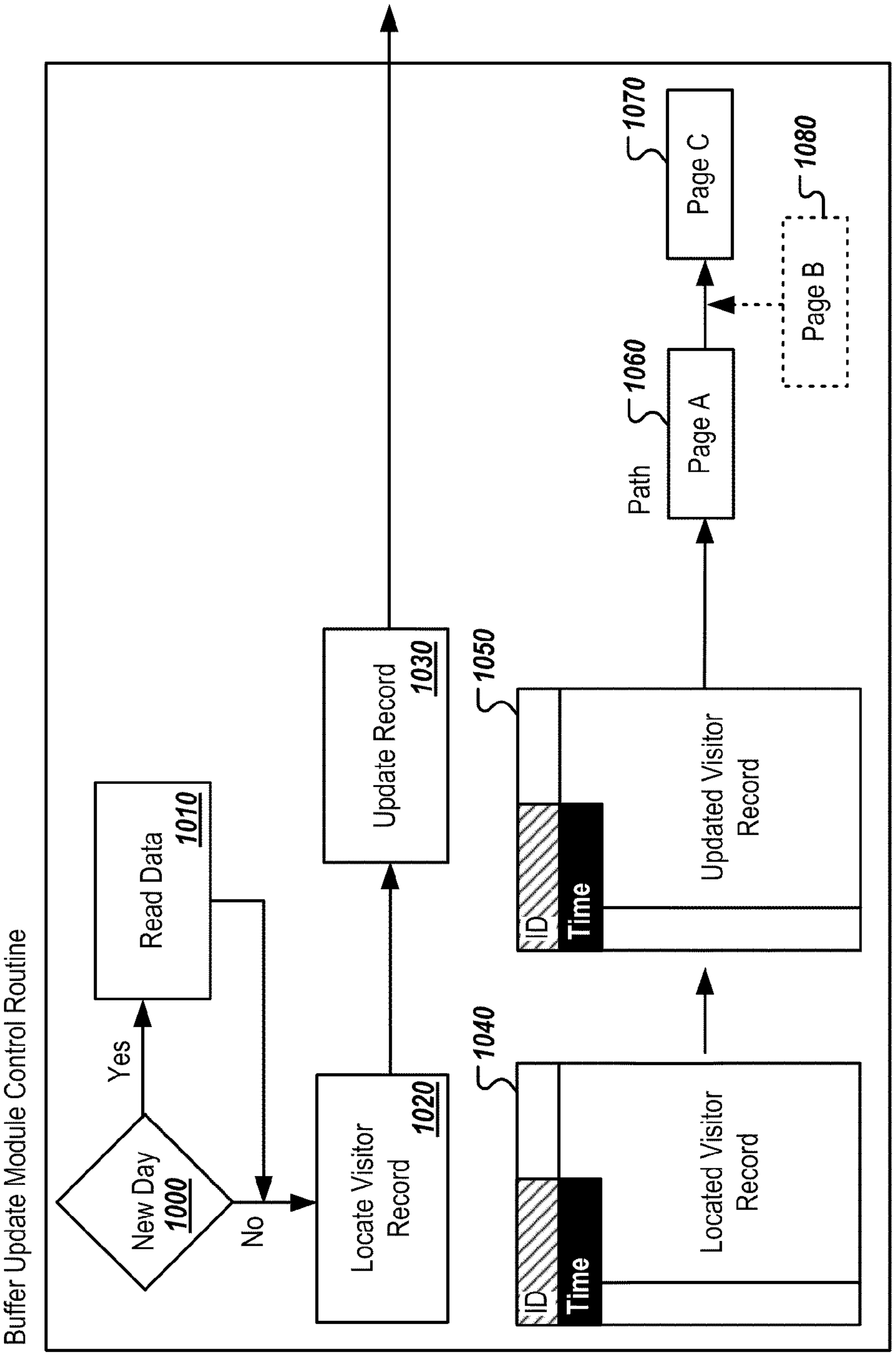
FIG. 8 is a flowchart and schematic diagram illustrating a preferred control routine for the buffer update module of FIG. 3.

FIG. 8 is a flowchart and schematic diagram illustrating a preferred control routine for the buffer update module 240 of FIG. 3. The control routine starts at step 1000, where it is determined if the log line 512 (hit) is from a new day by analyzing the timestamp 602''' of the log line 512. If the log line 512 is the first of a particular day, then control continues to step 1010. Otherwise, control jumps directly to step 1020.

At step 1010, the database buffer 260 is preloaded with any existing contents for that day from the actual database 300. Control then continues to step 1020.

At step 1020, the visitor record identified or created by the visitor identification module 230 is located in the database buffer 260. The located visitor record 1040 is shown schematically under the locate visitor record step shown in FIG. 8.

Control then continues to step 1030, where the located visitor record 1040 is updated and new information for that visitor is inserted into the located visitor record 1040. Traffic information is preferably updated for the visitor If the located visitor record 1040 is a new visitor record, then domain, referral, and browser information is preferably inserted into the located visitor record 1040. All visitors preferably have their path information updated with any new pageview information. The updated visitor record 1050 is shown schematically below the update record step 1030.

The timestamp 602''' of the log line 512 is used to determine the order of the events that took place. An illustrative example is shown in FIG. 8. In the example shown, a particular visitor is recorded as looking at Page A 1060 first and then Page C 1070. If the next log line 512 processed from the log file 510 indicates that the visitor looked at Page B 1080, the buffer update module 240 (at step 1030) checks the timestamp 602''' of the log line 512 to see where in the chain of events the page belongs. In the example shown, Page B 1080 occurred between Page A 1060 and Page C 1070. Thus, Page B 1080 is inserted into the visitor record between the Page A 1060 and Page C 1070. In this manner, the system 100 is able to update and correlate visitor data even if it is out of order in the log file 510.

This automatic processing of multiple log files 510 came from the discovery that a single multi-threading web server, such as Netscape, may not log all hits sequentially in time. Due to the nature of multi-threading applications, it is possible that a single log file 510 may contain hits out of chronological order. The system and method of the present invention was therefore designed to handle this situation properly by checking the timestamp 602''' of each log line 512 and inserting the information in the log line 512 into the appropriate place in the retrieved visitor record 1040 based on the chain of events. With this functionality, the processing of multiple load-balancing log files 510 is as simple as reading two log files instead of one.

The operation of the database buffer 260 will now be explained in more detail. As discussed above, the log engine 200 contains an internal database buffer 250 that mirrors part of the actual database 300, preferably in RAM. This allows the log engine 200 to correlate and update visitor records quickly for each hit without accessing the actual database 300 for each hit. Data is correlated and cached into the database buffer 250, which stores the data temporarily while processing the log file 510. When processing of the log file 510 is completed, the database buffer 250 is written back to the database 300 in one step.

The use of a database buffer 250 results in more RAM usage, but has the advantage of lowering the overhead of database access, resulting in faster processing times. By pre-inspecting the log files 510, the log engine 200 determines the time ranges being used and reads the appropriate data into the database buffer 250. The database buffer 250 allows Urchin to avoid reading and writing to the database 300 for each log line 512. Instead, the log engine 200 is able to make updates to the visitor tables 310 and the data tables 315 in memory (through the database buffer 250) and then read and write the entire data block to and from the database 300, which is preferably stored on disk, only once.

Database Buffer (250)

Figure 9:
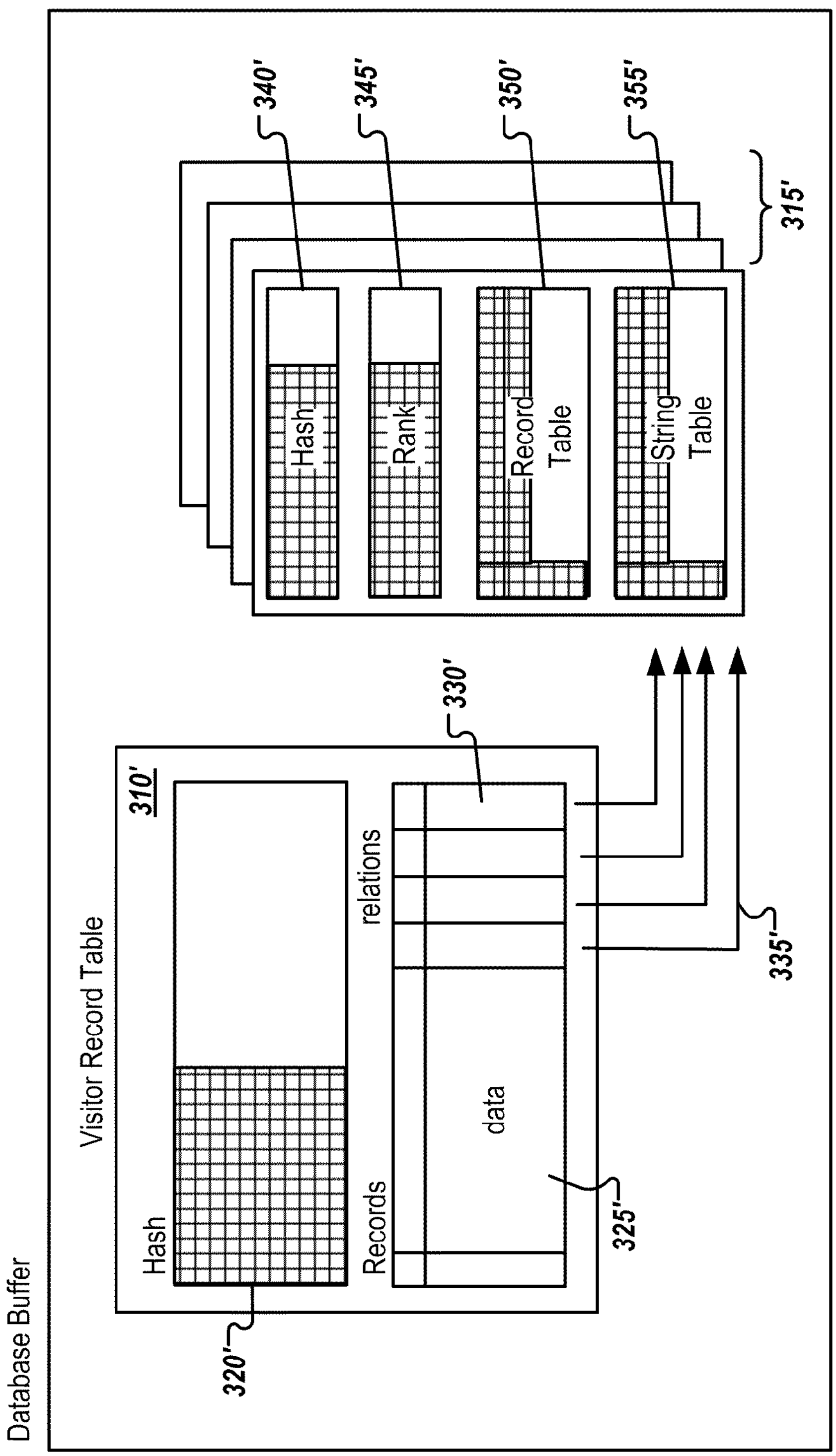
FIG. 9 is a schematic representation of the contents of the database buffer shown in FIG. 3.

FIG. 9 is a schematic representation of the contents of the database buffer 250. As discussed above, the database buffer 250 mirrors a portion of the database 300, preferably in RAM. Thus the visitor tables 310' and data tables 315' in the database buffer 250 have the same format as the visitor tables 310 and data tables 315 in the actual database 300.

Because the database buffer 250 is loaded with data from the database 300, the visitor tables 310' and data tables 340' in the database buffer 250 are also relational. The data is centered in the visitor table 310', creating a Visitor Centric Data Model. The visitor table 310' contains a partially filled hash table 320' that is used for quickly seeking visitor records. Below the partially filled hash table 310', the actual records 325' contain data about each visitor, such as hits, bytes, time, etc. Each unique visitor will have their own record in the visitor table 310'. As each log line 512 is processed and identified to a particular visitor, that visitor's record is updated in the visitor table 310' within the database buffer 250.

Like the visitor table 310 in the actual database 300, the visitor table 310' in the database buffer 250 is relational in nature and has a relations area 330' that contains pointers 335' to the data tables 315'. Like the data tables 315 in the actual database 300, each of the data tables 315' in the database buffer 250 store different visitor parameters such as domain, browser, and referral.

Each data table 315' contains a hash table 340', a rank table 345', a record table 350', and a string table 355'. The hash table 340' is used to seek records in the record table 350'. The rank table 345' is used to keep track of the top entries in the record table 350' based on the number of visitors using the parameter associated the data table 315'. This is useful for quick access to reports. The record table 350' stores the actual records within the data table 315' including the traffic information associated with the parameter associated with the data table 315'. The record table 350' does not store the value of the parameter. Instead, the record table 350' contains a pointer to a record in the string table 355'. Each of these subtables (320, 325, 330, 340, 345, 350, 355) has fixed width records allowing for efficient reading, writing, and copying of the entire data sets. In addition to the fixed width nature of the subtables, the records in the subtables are allocated in large blocks. Memory allocation is not necessary for each new record individually.

Besides using efficient hashing algorithms for processing the data, resizing of the database buffer 250 is done so that data tables 315' and the hash table 320' in the visitor table 310' are partially empty. This allows new records to be created instantly without allocating additional memory. The gray areas in the data tables 315' and the hash table 320' in the visitor table 310' indicate the used portions. As the tables reach a predetermined fullness threshold, they are preferably increased in size.

Once the processing of the log file 510 is complete, the data tables 315' and the visitor table 310' are written back into the actual stored database 300. The subtables are written separately so that empty records are not stored on the disk that holds the actual database 300. However, the fixed width nature of the subtables allows for efficient writing of entire blocks of data to the actual database 300. The use of the database buffer 250 increases the speed of the log engine 200 by avoiding frequent memory allocation and disk access. By caching information in volatile memory (in the form of the database buffer 250), and reading and writing fixed sized blocks of data, the log engine 200 is extremely fast.

DNS Resolver Module (260)

When a web server 500 receives a request for a web page, the web server 500 can either log the IP address of the visitor or it can use DNS to resolve the host and domain information of the visitor. While domain information is valuable for market analysis purposes, the resolution can add significant overhead to the web server 500 and delay the response of the web server to the end user. It is therefore desirable to pass the task of DNS resolving onto the system 100 of the present invention. This allows the web server 500 to stay as light and quick as possible for visitors accessing the website.

One of the biggest and most time consuming tasks in processing web server logs files 510 and creating valuable reports is the processing of the reverse DNS of the IP numbers. Each IP number must be converted to a host/domain name by using the distributed DNS system of the Internet. While the local name server may cache many of the answers, most will likely need to go out to the Internet for resolution.

The speed and scalability of the present system 100 is one of its advantages within the operations of large hosting companies. Whether processing single large websites or hundreds of thousands of small websites, the speed of the DNS resolver module 260 is important. The DNS resolver module 260 uses several innovative techniques for improving the speed and accuracy of the process, as will be described in more detail below.

For each IP number that needs resolving, a query is sent out to the Internet, where it bounces around a few times in the DNS system before coming back with the answer. This can take up to a couple of seconds, and sometimes the answer never comes back. As far as the local system is concerned, the bulk of this time is spent waiting for the response. An aspect of the present invention is the discovery that, since each of the queries is separate and unique, the processing can be done in parallel using multithreading techniques. The overall waiting can be done all at once instead of sequentially, thus shortening the overall processing considerably.

For example, if ten queries are each resolved in one second each, normal overall processing time would be ten seconds. However, by making the operation parallel so that all ten queries are processed simultaneously, then the overall processing time could be reduced to one second.

In practice, however, multithreading systems, such as those based on the use of POSIX threads and BIND 8.2, carry a significant overhead, and the setting up of sockets and memory locking reduces the benefits of the multithreading. Instead, the DNS resolver module 260 is not based on threads, but takes on the advantage of the parallel nature of the underlying protocols themselves to simulate threading operation without the additional overhead. Besides improving the overall speed and accuracy, the porting of the software is simplified, as it depends on less library calls.

The DNS resolver module 260 generally uses the User Datagram Protocol (UDP) on top of the IP network protocol. The UDP protocol has inherent parallel capabilities. Each query in the protocol is sent like a letter and uses a connectionless socket. Thus, multiple queries can be sent simultaneously without waiting for responses. Multiple responses can be received at any time and in any order. There is no guarantee that all the answers will return or that they will appear in any particular order. But, as long as the queries are tracked with an ID number, this UDP protocol can be used effectively to parallelize the DNS resolving operation without the overhead of threads.

Figure 10:
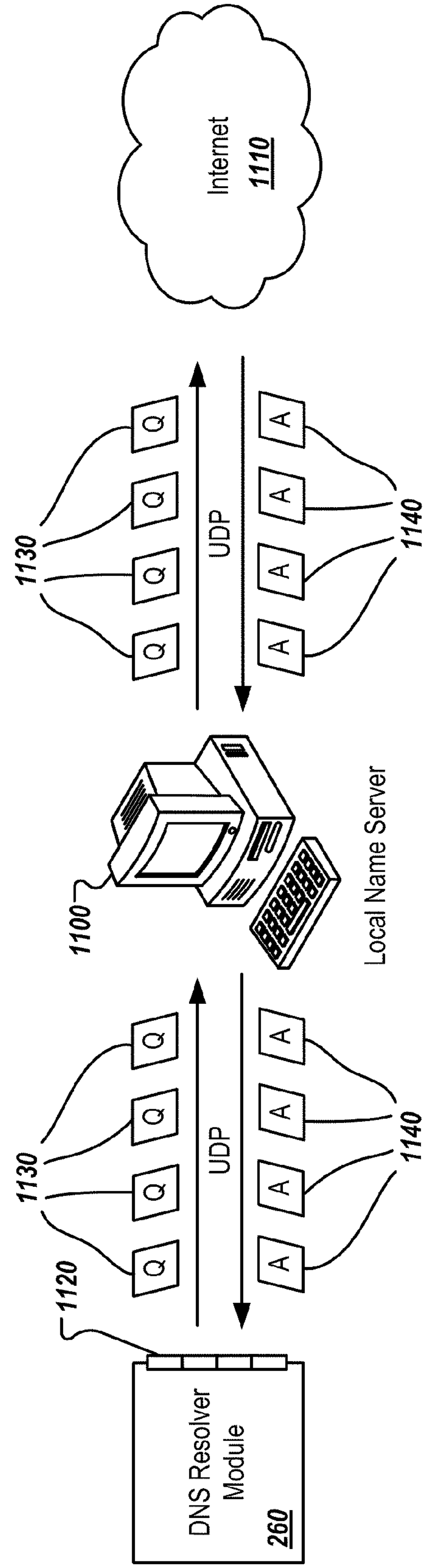
FIG. 10 is a schematic diagram illustrating the operation of the DNS resolver module of FIG. 3.

FIG. 10 is a schematic diagram of illustrating the operation of the DNS resolver module 260. The DNS resolver module 260 communicates with a local name server 1100. The local name server 1100 is part of the Internet 1110 DNS system, but resides in the local network as a primary cacheing name server acting as a relay between the DNS resolver module 260 and the multiple DNS servers in the Internet 1110.

The communication between the DNS resolver module 260 and the local name server uses several UDP sockets 1120. The UDP sockets 1120 are setup and destroyed only once. Once the UDP sockets 1120 are established, the DNS resolver module 260 sends groups of queries 1130. The queries 1130 are represented by "Q" boxes, and the responses (or answers) 1140 are represented by "A" boxes. The local name server 1100 relays the queries 1130 and answers 1140 to the Internet 1110 using a built-in DNS system. The local name server has cacheing ability and will remember recently asked queries 1130 and answer immediately instead of sending them on to the Internet 1110.

One of the keys to shortening the processing time is to get as many queries 1130 out in the Internet 1110 at one time. This shortens the waiting significantly. Without the use of threads, the DNS resolver module 260 takes advantage of the UDP protocol, and goes through a loop of sending and reading queries 1130 and answers 1140, as will be described in more detail below. Without waiting for all answers 1140 to return or for thread controls to be freed up, the DNS resolver module preferably sends as many queries 1130 as possible out into the Internet 1110.

As incoming answers 1140 are decoded and the ID numbers are matched with the originating queries 1130, the IP numbers are efficiently resolved in a manner that truly parallelizes the waiting and thus dramatically reduces the processing time without the overhead of threads.

During the flood of queries 1130 and answers 1140, the DNS resolver module 260 goes through a primary loop of sending queries 1130 and reading answers 1140. The kernel level sockets and the local name server 1100 can only handle so many requests simultaneously, and will drop excess queries 1130 if capacity is reached. While having a few (i.e., less than 10%) of the queries 1130 dropped is acceptable, having too many queries 1130 dropped will result in a large percentage of retries, creating additional work and actually slowing the overall processing time. However, it is desirable to send queries 1130 as rapidly as possible. What is needed is a feedback loop that can adjust the rate at which queries 1130 are sent and the waiting time for answers 1140.

Figure 11:
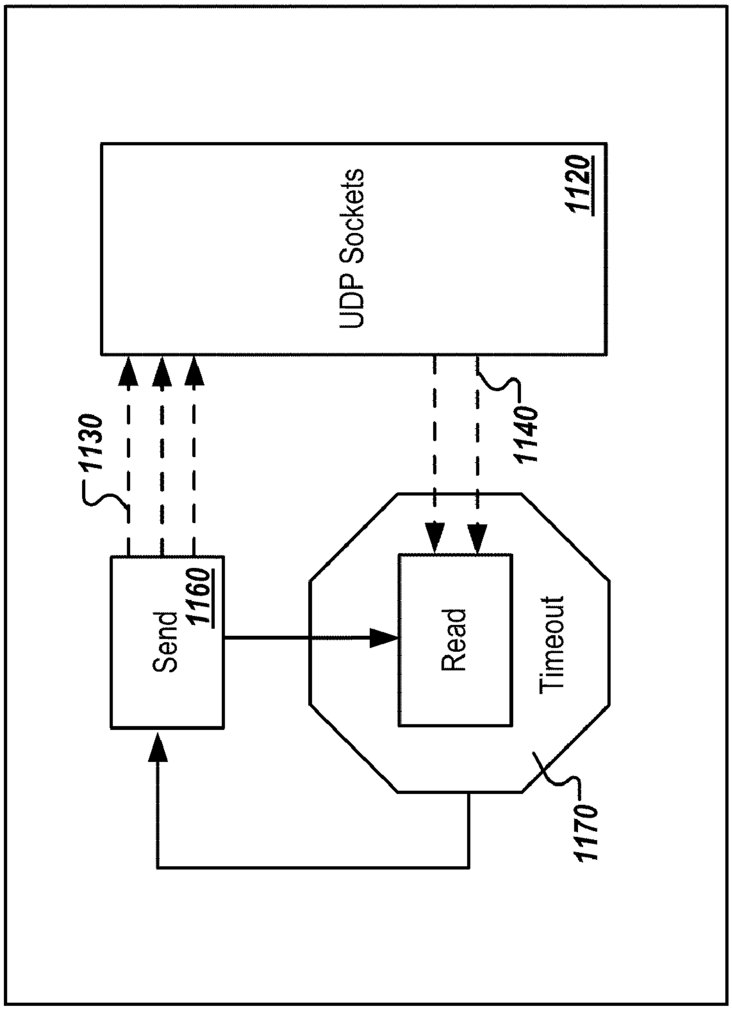
FIG. 11 is a flowchart and schematic diagram of a feedback loop control routine preferably used by the DNS resolver module of FIG. 3.

FIG. 11 is a flowchart and schematic diagram of a feedback loop control routine preferably used by the DNS resolver module 260. A resolver loop 1150 controls a loop that cycles between sending and reading queries 1130 and answers 1140.

The control routine starts at step 1160, where a group of queries 1130 are sent through the UDP sockets 1120. Once the queries 1130 are sent, control continues to step 1170, where the resolver loop 1150 will try reading answers 1140 for a predetermined amount of time (Timeout). Once the Timeout is reached, the resolver loop will compare how many queries 1130 were sent against how many answers 1140 were received, and adjust the Timeout accordingly. Control then returns to step 1160.

In addition to the socket speed capabilities, certain queries 1130 will inherently take longer than others. Some queries 1130 may need to go halfway around the world before resolving is completed. To minimize this effect, The resolver loop 1150 preferably begins with a very aggressive (short) Timeout, and progressively increases the Timeout to wait for the answers 1140 that are taking longer to arrive. The resolver loop 1150 will actually go through multiple loops and, at a slower pace, reattempt queries 1130 that were never answered. This adaptable resolving speed control gives the DNS resolver module 260 the ability to process the bulk of queries 1130 very quickly, and minimize the impact of a few slow or non-responding answers 1140.

The DNS resolver module 260 is preferably configured with the ability to increase the resolving percentage and overall accuracy of the DNS resolving module 260 by adapting the query level. Under normal DNS resolving, the IP number is mapped to a specific hostname. For example, the IP number 202.110.52.16 may map to the hostname:

dial141-sddc2.npop43.aol.com

While it may be interesting to see the "dial141-sddc2.npop43" part of the hostname, one is typically only interested in the domain part (e.g., "aol.com"™) of the answer 1140. The first part of the answer 1140 is specific to each provider and does not contribute to the demographic-type reporting that the present system 100 is preferably designed to provide.

In many networks, especially government, military, and small private networks, individuals IPs are not always mapped to anything. The query 1130 of a specific IP may return with an answer 1140 of "unknown host", which means that not all if the IPs were mapped back to the hostnames. Unfortunately this can reduce the resolving percentage by 20 or 30 percent, and skew the demographic data away from non-resolvable networks such as are often found in government, military, and educational networks.

To make up for this deficiency, the DNS resolving module 260 preferably deploys an adaptable resolving level mechanism that attempts to find out who controls the network in question if the hostname answer 1140 returns unsuccessfully.

Figure 12:
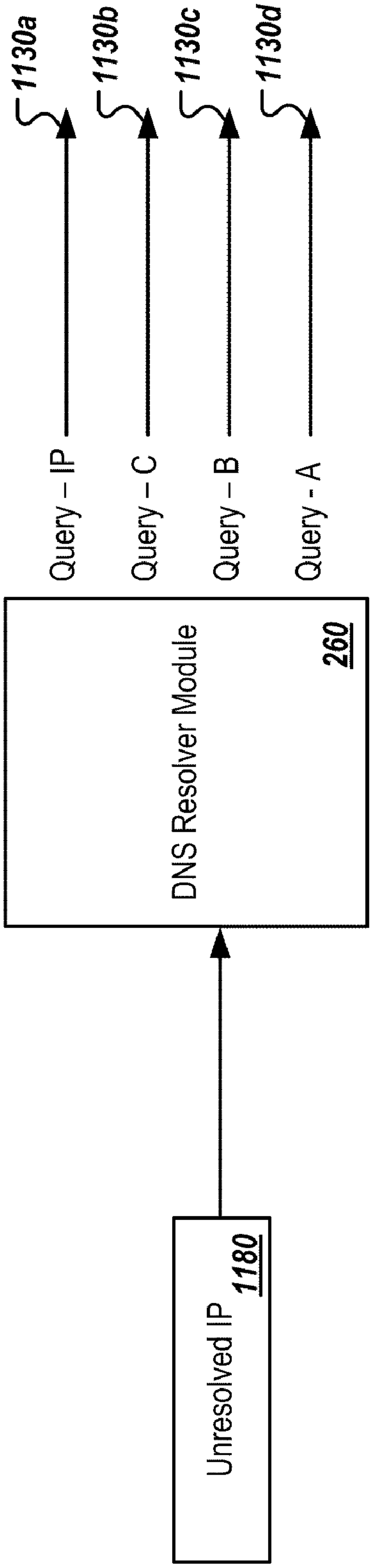
FIG. 12 is a schematic diagram of how a preferred embodiment of an adaptable resolution mechanism in the DNS resolver module operates.

FIG. 12 is a schematic diagram of how a preferred embodiment of the adaptable resolution mechanism operates. An unresolved IP number 1180 enters the DNS resolver module 260. The DNS resolver module 260 will make multiple attempts at resolving the IP number by sending out multiple queries 1130 one at a time using different query information. The first query 1130*a* will attempt to resolve the entire specific IP number. If that returns unsuccessful, then a second query 1130*b* will attempt to resolve the Class-C network address (a Class-C network address is equivalent to the first three parts of an IP address).

If the second query returns unsuccessful, a third query 1130*c* will attempt to resolve the Class-B network address. If the third query is unsuccessful, a fourth query 1130*d* will attempt to resolve the Class-A network address. Many times, the Class-C or Class-B network addresses will resolve correctly when the IP address did not.

This technique improves the resolving accuracy dramatically and improves overall performance speed. In the case of government, military, educational and other private networks, "unresolved" percentages have been observed to go from 35% down to 8%, and "k12.us" and "navy.mil" show up in the top domains reports using the adaptable resolving level mechanism of the present invention. While these domains are not resolving their individual IPs, the general source of the traffic is obtained.

Figure 13:
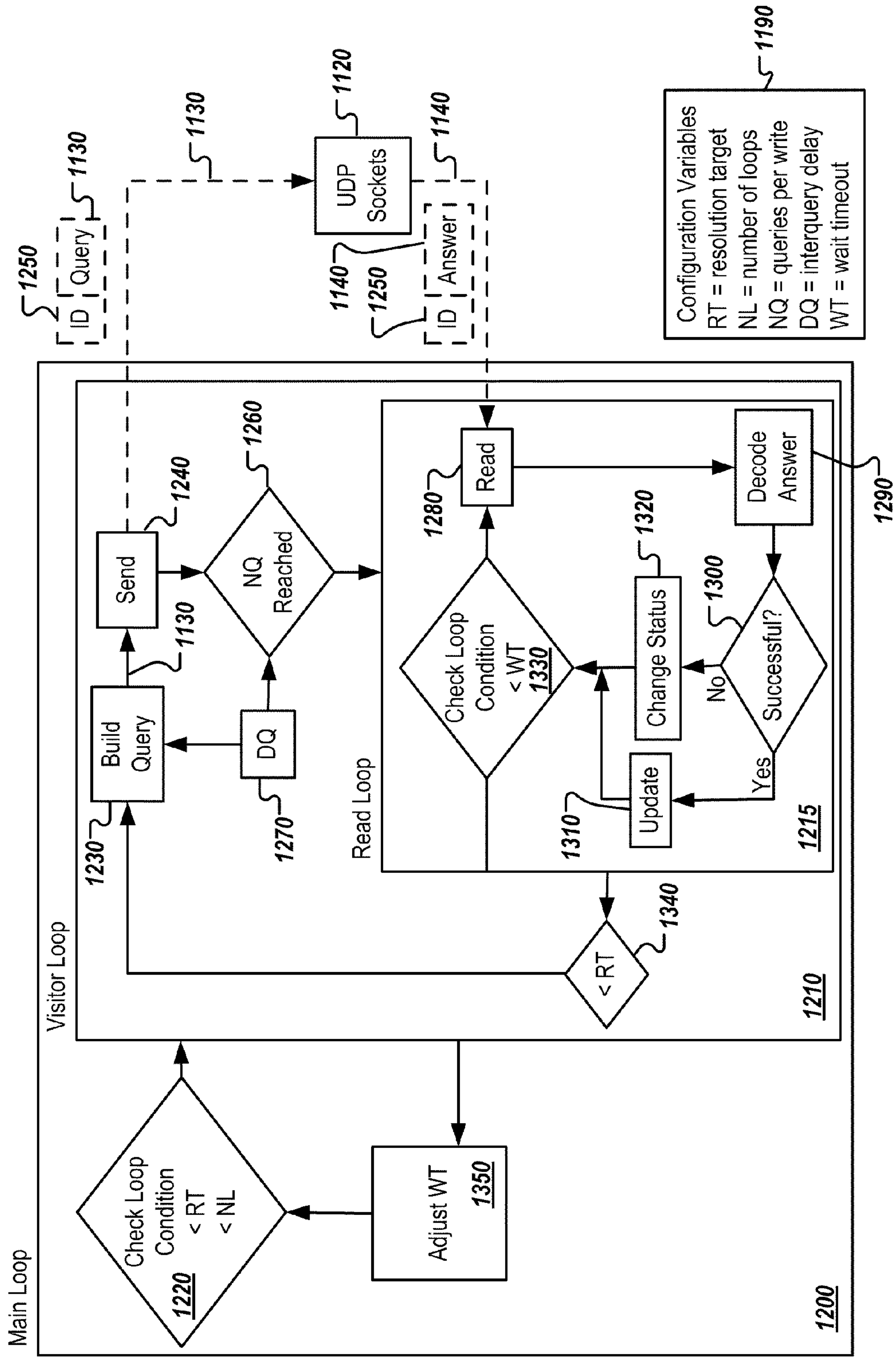
FIG. 13 is a flowchart of preferred control routines for various control loops within the DNS resolver module of FIG. 3.

Using the above-described techniques, the DNS resolver module comprises a nested-loop, adaptable system that is fast and efficient. The nested-loop architecture is shown in FIG. 13, which is a flowchart of a preferred control routine for the various loops within the DNS resolver module 260.

The control routine begins by initializing some variables, including five configuration variables 1190 that include:

resolution target (RT);
number of loops (NL);
queries per write (NQ);
interquery delay (DQ); and
wait timeout (WT).

These five settings represent starting points for operation. They may be modified at runtime using the feedback mechanism discussed above in connection with FIG. 11. The control routine comprises a main loop 1200, a visitor loop 1210 nested within the main loop 1200, and a read loop 1215 nested within the visitor loop 1210. Dashed lines indicate asynchronous non-loop flow tasks. Sockets are initialized before the main loop 1200 begins.

The control routine begins at step 1220, where it is determined if the loop should continue. The loop 1200 will continue as long as the "number of loops" (NL) has not been reached and the "resolution target" (RT) has not been reached. NL is incremented once the loop begins and RT is adjusted after each "decode answer" step 1290, which will be described below.

The NL and RT variables serve an important purpose. They allow a high resolving target to be set, while setting an ultimate timeout. Depending on the size of the data, the number of sites, and the amount of time available, system administrators can modify these variables before operation. Once the resolution target, or the number of loops NL, is reached, the control routine will exit and clean up.

If NL and RT have not been reached, control continues to the visitor loop 1210, whose purpose is to build and send queries for each unresolved visitor in the visitor table 310'. The visitor loop 1210 starts at step 1230, where the next unresolved visitor record from the visitor table 310' is pulled and a query 1130 is built. An ID number 1250 from the visitor table 310' is used in the building of the query 1130 so that it can be tracked later on as a response.

Next, at step 1240, the query 1130 is sent to the UDP sockets 1120. The UDP sockets 1120 are used in round robin fashion which allows minimizes the waiting for buffer controls.

A counter keeps track of how many queries 1130 have been sent in the current batch. Control then continues to step 1260, where the counter is checked against the NQ variable. If NQ has not been reached, control loops back to step 1230. An optional interquery delay (DQ) step 1270 can be inserted between steps 1260 and 1230 to keep the visitor loop 1210 from running too fast.

If NQ has been reached, which occurs when all the queries in the batch have been sent, NQ is reset and control then continues to the read loop 1215. The read loop 1215 continues until the WT timeout variable is reached.

At step 1280, any buffered incoming answers 1140 are read from the UDP sockets 1120. Next, at step 1290, each answer 1140 is decoded. Control then continues to step 1300.

At step 1300, it is determined if the answer 1140 is successful. If the answer 1140 is successful, control continues to step 1310, where the visitor table 310' is updated with the domain information. Control then continues to step 1330.

If, at step 1300, it is determined that the answer 1140 is unsuccessful, control continues to step 1320, where the record in the visitor table 310' is modified by changing the resolution status. The resolution status is used to control the resolution level, as discussed above. If the answer 1140 comes back as "unknown" then the resolution status is changed for that visitor record, indicating that the next query 1130 should attempt to resolve the larger network instead of the specific IP. Control then continues to step 1330.

At step 1330, the read loop 1215 condition is checked by determining if the incoming UDP sockets 1120 are empty and if the timeout WT has been reached. If the incoming UDP sockets 1120 are empty and the WT timeout has been reached, the read loop 1215 ends, and control flows back to the visitor loop 1210 at step 1340. Otherwise, the read loop 1215 continues, and control loops back to step 1280.

At step 1340, it is determined if the resolution target (RT) has been reached. If it has, the visitor loop 1210 ends, and control flows back to the main loop 1200 at step 1350. Otherwise, the visitor loop 1210 continues at step 1230 with the next batch of unresolved queries.

At step 1350 of the main loop 1200, the WT timeout is adjusted (increased for the next loop). Control then continues to step 1220, where NL and RT are checked, NL is incremented and starts the entire process over again if neither NL nor RT have been reached.

With minimal overhead, the DNS resolver module 260 takes advantage of the UDP protocol and maximizes the parallelization of the processing. Through a series of nested loops and control parameters, the DNS resolver loop is able to adapt both speed and level in order to meet the resolving target as quickly as possible. Multiple rounds and levels of queries 1130 are resent to cover lost or failed attempts, thereby increasing overall accuracy and resolution percentage dramatically. Thus, system administrators can put a cap on overall processing time, while maintaining a high resolution target.

Database Update Module (270)

Once the log file processing is complete and all the log lines 512 (hits) are represented in the visitor table 310' on the database buffer 250, the visitor table 310' is sorted (if multiple websites are represented). The database buffer 250 is outputted to the database 300 using the database update module 270.

Figure 14:
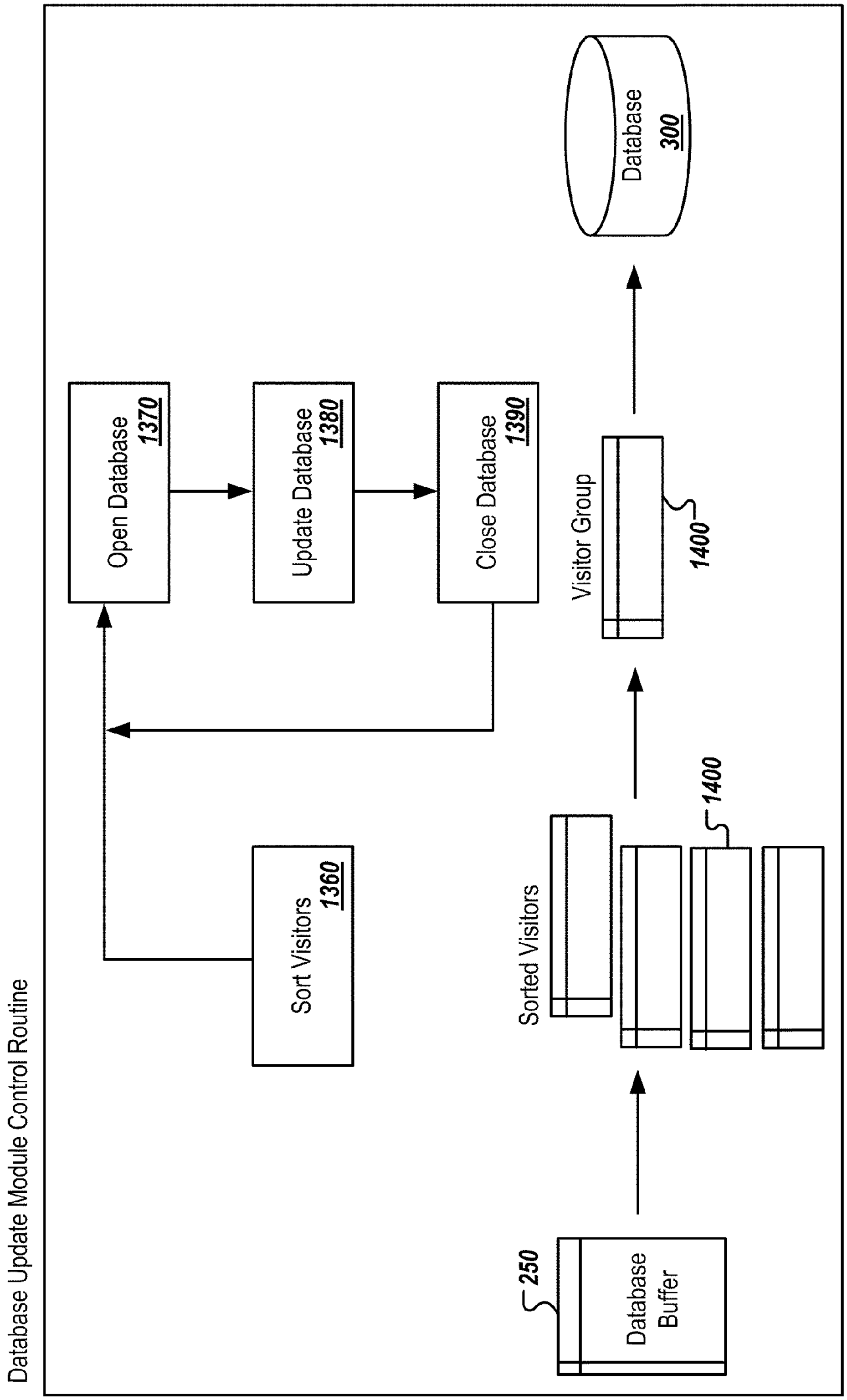
FIG. 14 is a flowchart and schematic diagram illustrating a preferred control routine for the database update module of FIG. 3.

FIG. 14 is a flowchart and schematic diagram illustrating a preferred control routine for the database update module 270. The schematic diagram below the control routine steps illustrates what is occurring to the data during the control routine.

The control routine starts at step 1360, where the visitors in the database buffer 250 are sorted based on their associated website identification. Preferably using a quicksort algorithm, the records in the database buffer 250 are sorted into groups that belong to the same website. If only one website is represented by the log file 510, then step 1360 is trivial. However, in the case of multiple websites, the database buffer 250 is sorted into groups of visitors.

The control routine then continues to step 1370, where the database 300 is opened. Then, at step 1380, the database 300 is updated with the data in one of the visitor groups 1400. The process then continues to step 1390, where the database 300 is closed.

The control routine then loops back to step 1370, and the database update process is repeated for each visitor group 1400. By processing the records in groups, the overhead created by accessing the database 300 is reduced.

Database (300)

Figure 15:
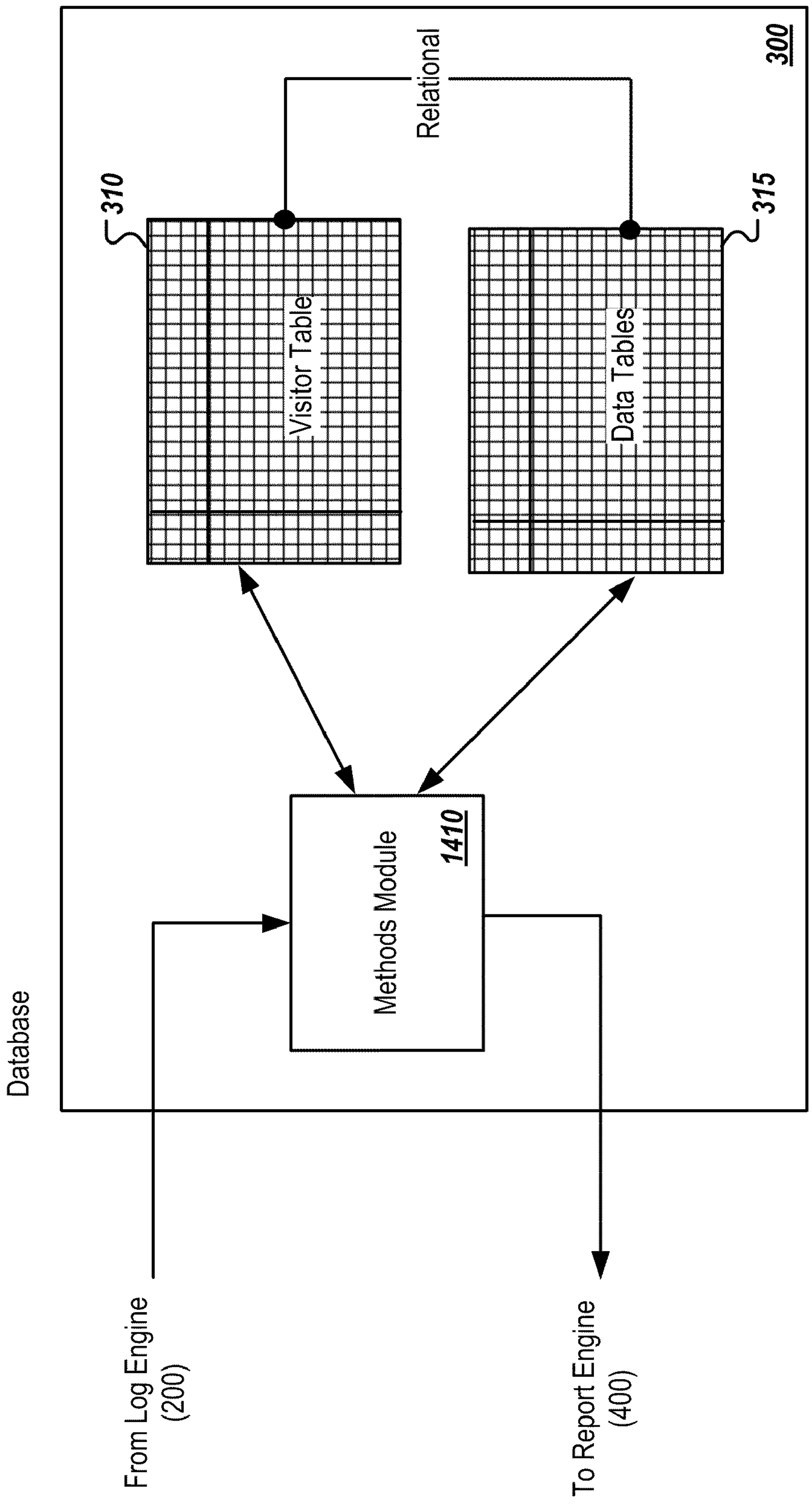
FIG. 15 is a schematic diagram illustrating the main components of the database shown in FIG. 1.

FIG. 15 is a schematic diagram illustrating the main components of the database 300. As discussed above, the database 300 contains a visitor table 310 and data tables 315. The structure is relational in nature as the visitor table 310 relates to information stored in the data tables 315.

The database 300 also includes methods module 1410 that provides an interface for accessing, seeking, and inserting data into the visitor and data tables 310 and 315. Both the log engine 200 and the report engine 400 access the methods module 1410.

The methods module 1410 is the only module that is allowed to directly access the data in the database 300. This creates a modularity to the database 300, in which the format of the visitor table 310 and/or the data tables 315 can be modified without changing the interface to the other modules in the system 100.

Report Engine

As ISPs add thousands of web sites to a single system, the creation of reports can begin to take as long as processing the data. With an ever increasing number of reports to create, the disk space and time needed to accomplish this side of the task can become a problem. The report engine 400 provides a centralized system that contains a single copy of the report templates and icons needed to generate reports, and delivers specific reports for a particular web site only when requested.

The report engine 400 only stores the data for each web site, and not the specific reports. Since the reports are web-based, they can be delivered on the fly as requested through the Common Gateway Interface (CGI) of the web server.

Figure 16:
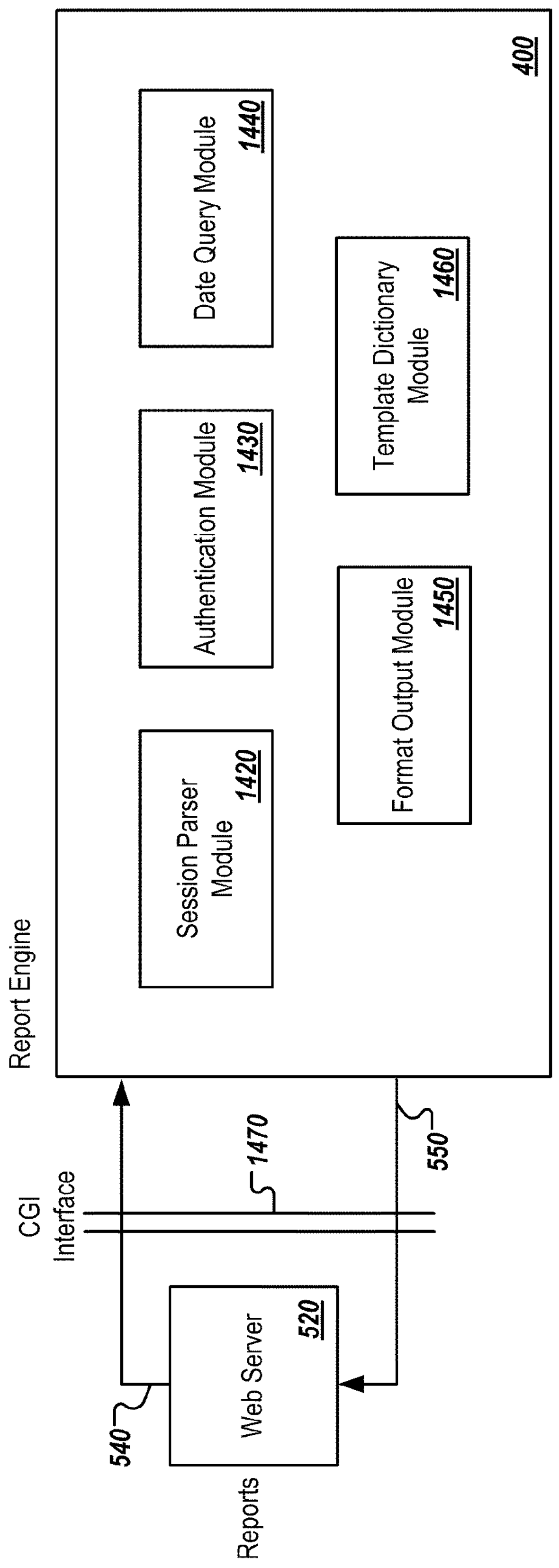
FIG. 16 is a schematic diagram of a preferred embodiment of the report engine of FIG. 1.

FIG. 16 is a schematic diagram of a preferred embodiment of the report engine 400. The report engine 400 comprises a session parser module 1420, an authentication module 1430, a data query module 1440, an format output module 1450 and a template/dictionary module 1460.

In operation, a report request 540 received by the web server 520 from an end-user is sent by the web server 520 to the report engine 400 through the Common Gateway Interface (CGI) 1470 of the web server 520. The CGI 1470 is a standard mechanism for web servers to allow an application to process input and deliver content dynamically via the web.

The session parser module 1420 reads the input from the report request 540 and sets internal variables accordingly. The variables are then used to determine the data to use, the report to create, and the format of delivery.

The authentication module 1430 verifies that the end-user that sent the report request has permission to view the requested report. Upon verification, the data query module 1440 queries the database 300 for the raw data needed to generate the requested report.

The raw data is passed to the format output module 1450, which uses a set of templates from the template/dictionary module 1460 to format and create the report 550 to be sent back to the end-user via the web server 520. The use of templates and dictionaries in the template module allows for easy customization of the reporting format. Templates can be used to change branding and the overall look and feel of the report interface. Dictionaries in the template/dictionary module 1460 can be used to change the report language on the fly. The end-user can toggle which dictionary is used for reporting directly through the CGI interface 1470.

The access and delivery of reports is preferably controlled using a Javascript application, which is preferably delivered to the end-user upon the first report request 540. The Javascript Application provides the mechanisms for displaying report content and querying for new reports.

The operation of each of the modules in the report engine 400 will now be explained in more detail.

Session Parser Module (1420)

The session parser module 1420 is used to read and access data specific to the type of request being made. Furthermore, hosting operations are creating control panel interfaces with which customers can login and access all of their tools and applications from one web-based location. Customers login once into the control panel, and then have access to e-mail, website builder tools, newsgroups, etc.

In order to integrate the present system 100 into custom control panel interfaces, the session parser module 1420 is a flexible session sensitive system that allows the present system 100 to work seamlessly with the user's control panel.

Figure 17:
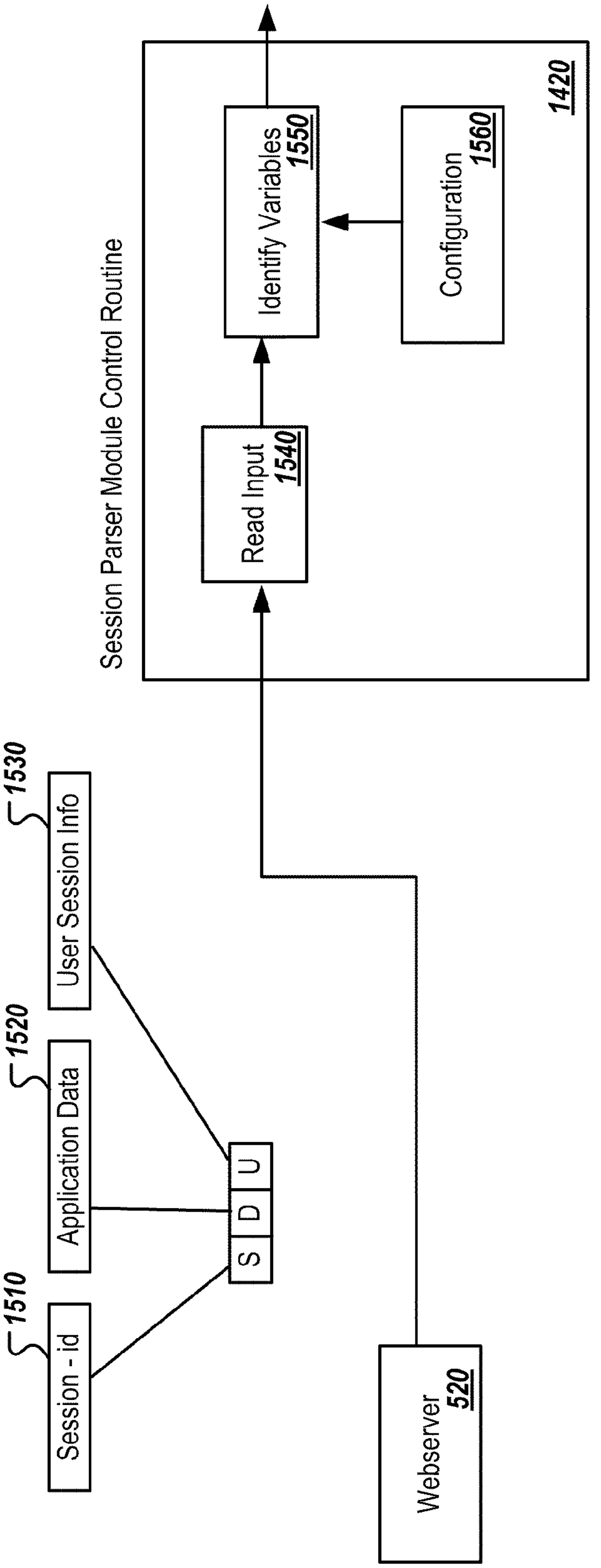
FIG. 17 is a flowchart of a preferred control routine for the session parser module of FIG. 16.

FIG. 17 is a flowchart and schematic diagram of a preferred control routine for the session parser module of FIG. 16. User requests for reports are generated and passed to the report engine 400 from the web server 520. Since the system 100 only contains one report engine 400, parameters 1500 are passed to the session parser module 1420 within the report engine 400 in order to determine which report to generate. The passing of parameters 1500 is built into the navigation of the reporting interface, i.e., as the end-user clicks through the navigation menus within the interface and selects a report, the proper parameters 1500 are automatically sent to the session parser module 1420.

The parameters 1500 preferably contain three parts. The session-id 1510 is used to keep track of which user is logged into the system. The application data 1520 contains the report-specific parameters used to select the correct report. The user session info is an optional set of parameters that can be used to integrate the system 100 into a user control panel containing multiple applications.

The control routine 1420 begins at step with the read input step 1540, which parses the list of parameters 1500 and separates the data into "name-value pairs." Control then passes to the identify variables step 1550, which uses a pre-determined configuration 1560 to match the external name-value pairs with internal variables. This allows the system 100 to recognize custom variables being used by proprietary control panels and other user interface mechanisms.

Authentication Module (1430)

Figure 18:
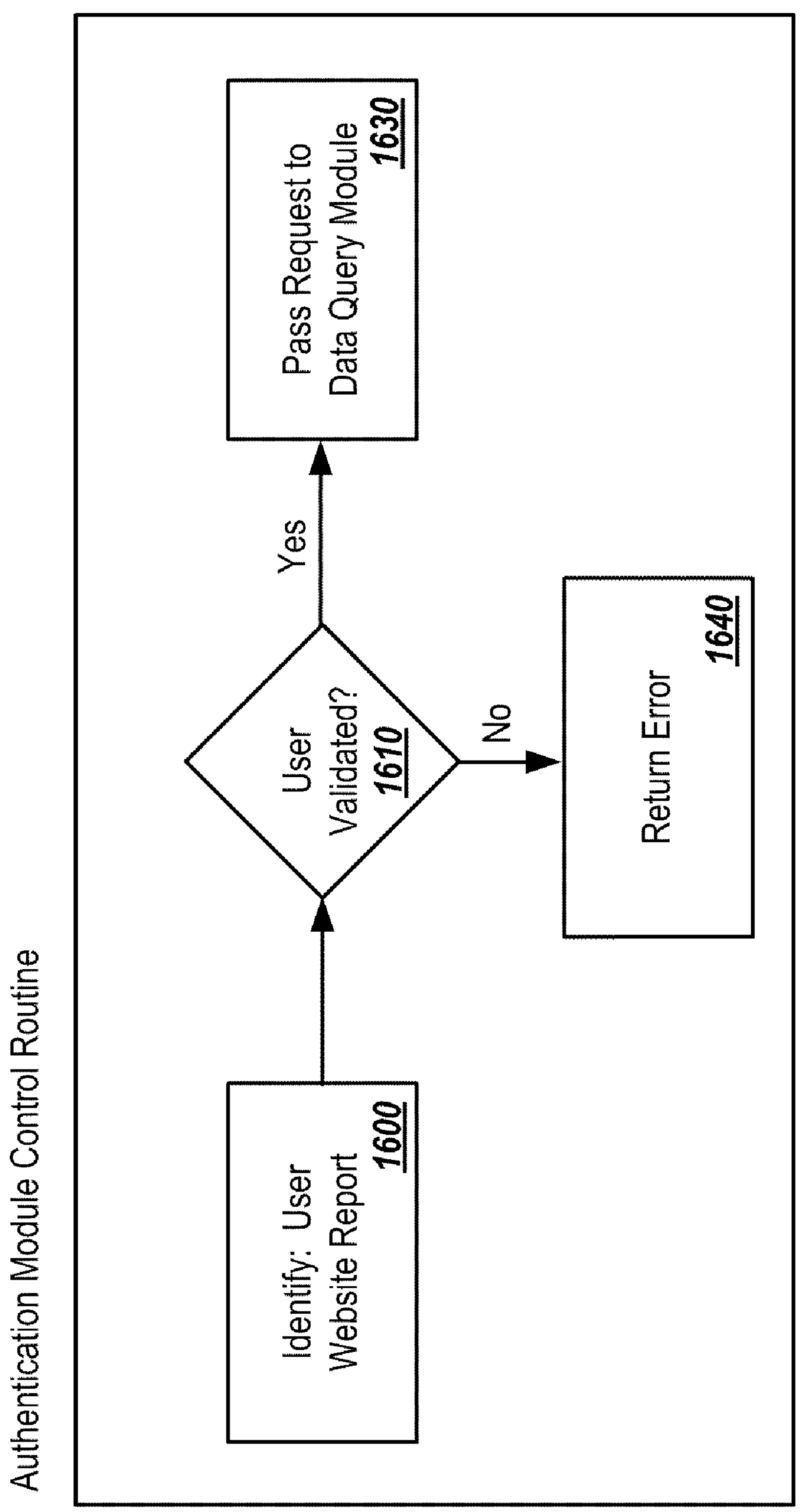
FIG. 18 is a flowchart of a preferred control routine for the authentication module of FIG. 16.

FIG. 18 is a flowchart of a preferred control routine for the authentication module 1430. After the specific variables of the report request and session are determined, the authentication module 1430 provides a flexible way to check access authorization for report requesters. While the authentication module 1430 may user either built in functionality or access pre-existing user databases, the basic steps of the control routine are the same.

The control routine starts at step 1600, where the identity of the user, the website and the report being requested are determined based on data from the session parser module 1420. The control routine then continues to step 1610, where the validation of the user is performed.

Based on configuration, step 1610 can either access internal configuration parameters, listing users and reports, or it can access an external source (not shown) for user validation. If the user is validated for the report request, then control continues to step 1630, where the report request is passed to the data query module 1440. If the validation fails, control jumps to step 1640, where an error response is returned to the user.

Data Query Module (1440)

Figure 19:
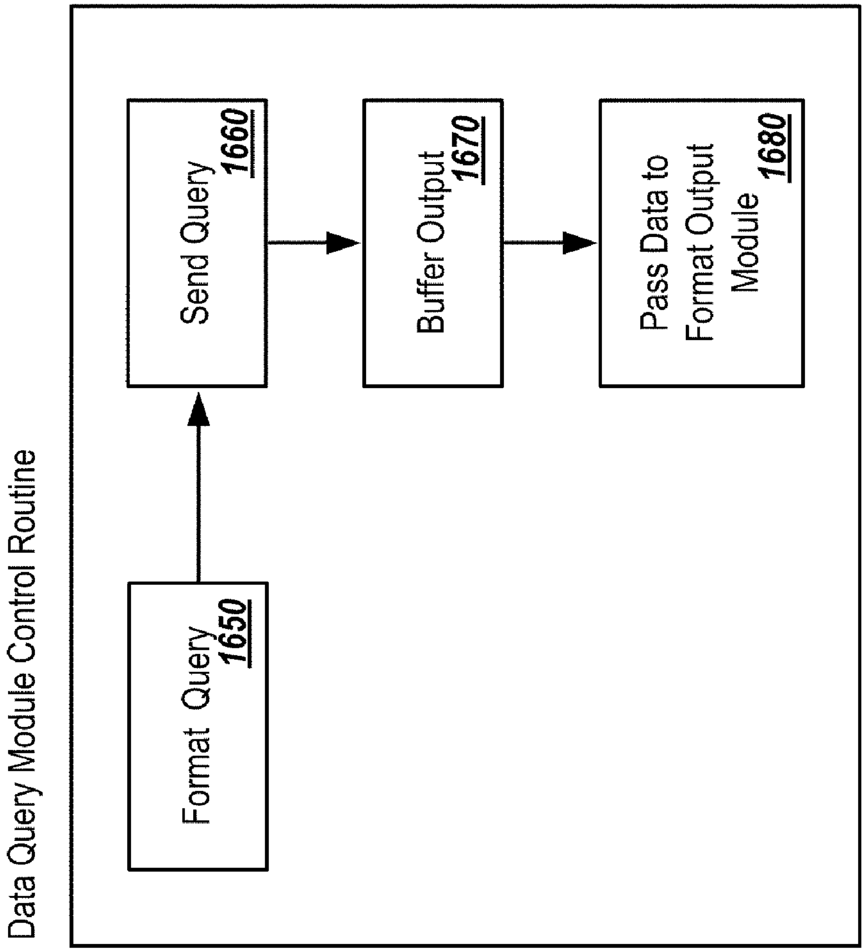
FIG. 19 is a flowchart of a preferred control routine for the data query module of FIG. 16.

FIG. 19 is a flowchart of a preferred control routine for the data query module 1440. This data query module 1440 accesses the methods module 1410 in the database 300 in order to receive a report-ready raw data set.

The control routine starts at step 1650, where the identification of the requested report and other parameters parsed previously by the session parser module 1420 are formatted into a query that can be passed to the database 300. The format of the query is based on the specification of the methods module 1410 in the database 300. Typically, SQL type queries are created at step 1650.

Next, at step 1660, the query generated at step 1650 is sent to the database 300. Then, at step 1670, the data from the database 300 is received and stored in a buffer. The buffer now contains the raw unformatted data for the requested report. Control then continues to step 1680, where the data received and stored in the buffer is passed to the format output module.

Format Output Module (1450)

Figure 20:
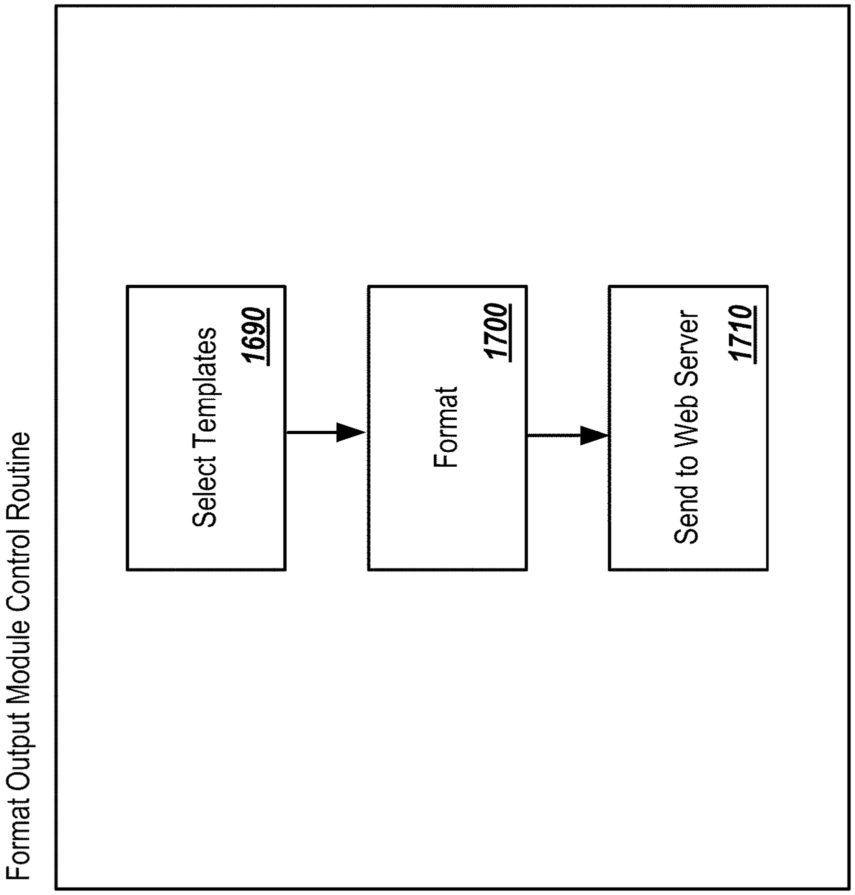
FIG. 20 is a flowchart of a preferred control routine for the format output module of FIG. 16.

FIG. 20 is a flowchart of a preferred control routine for the format output module 1450. The control routine starts at step 1690, where templates and dictionaries are obtained from the template/dictionary module 1460. The templates and dictionaries are chosen based on the type of report and language desired.

Control then continues to step 1700, where the requested report is formatted by merging the data stored in the buffer by the data query module 1440 with the chosen templates and dictionaries. Variables are replaced with values, and words are replaced with dictionary entries. The result is a web-based report ready for delivery custom created for each user. The report is delivered to the user at step 1710.

Javascript System

The report engine 400 preferably uses a Javascript system comprising a special combination of HTML and Javascript to produce interactive reports that are extremely efficient and easy to use. The basic concept is that the Javascript, which is loaded into the user's web browser contains the code necessary to create the visual reports. Once loaded, the web server 520 only needs to deliver data to the web browser, which is then rendered on the user side of the Javascript system.

The benefits of Javascript system are less connections to the web server 520. The user can experience real-time navigation, as many of the controls do not require new connections to the web server 520. Opening menus and sorting data occur directly in the web browser. Used in conjunction with the CGI Reporting technology described previously, the Javascript system is extremely efficient and scalable for even the most crowded web server communities.

Figure 21:
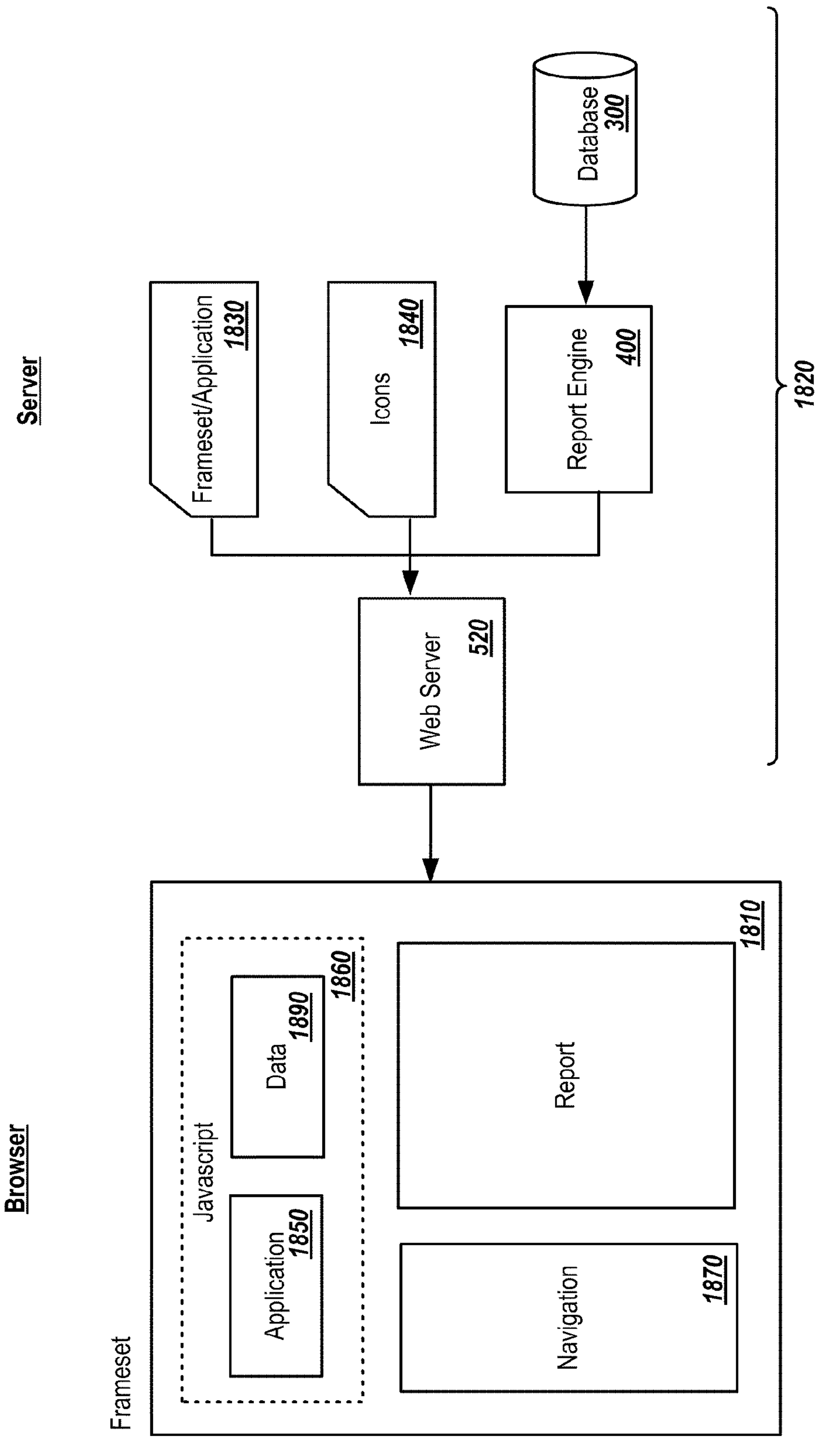
FIG. 21 is a schematic diagram of a preferred embodiment of a Javascript system used by the report engine of FIG. 16.

FIG. 21 is a schematic diagram of a preferred embodiment of the Javascript system. The system comprises an end-user web browser side 1810 and a server side 1820.

When the end-user first accesses the report engine 400, the report request is sent to the web server 520 which returns the frameset/application 1830 and icons 1840. A Javascript application 1850 resides hidden in the parent frameset 1860. The Javascript application 1850 then draws the two frames: the navigation frame 1870 and the report frame 1880. The navigation frame 1870 is drawn directly from the Javascript application 1850.

As the end-user wants to see a different attribute of the report or data, they can click on navigational and control elements in either the navigation frame 1870 or the report frame 1880. These control elements affect variables in the code of the frameset 1860, which then redraws the necessary subframes. If the end-user has selected something that requires a new data set, only the data is requested and delivered from the web server 520 through the report engine 400. The Javascript application 1850 loads the new data 1890, and draws the subframes and reports accordingly.

Real-Time Reporting

The demand for real-time reporting comes from many sources. In today's fast-paced economy, marketing and advertising managers wish to make rapid decisions and have immediate access to data as it occurs. Likewise, webmasters and system administrators, who are charged with managing critical website systems and servers, need real-time monitoring tools in order to keep a finger on the pulse of their systems. The ability to monitor activity in real-time gives the system administrators the ability to react to problems and potential attacks. Likewise, managers can monitor marketing strategies and ad campaign effectiveness as they are released.

As described previously, the system 100, using the live data access control routine shown in FIG. 5, has the ability to record web traffic into the database 300 continuously as it occurs. Since, as describe above, the report engine 400 creates reports when they are requested, all reports can display up-to-date real-time information. In addition to general demographic and statistical reports, the system 100 is preferably configured to create a series of reports that are specifically designed to take advantage of real-time data.

Visitor Monitor

Figure 22:
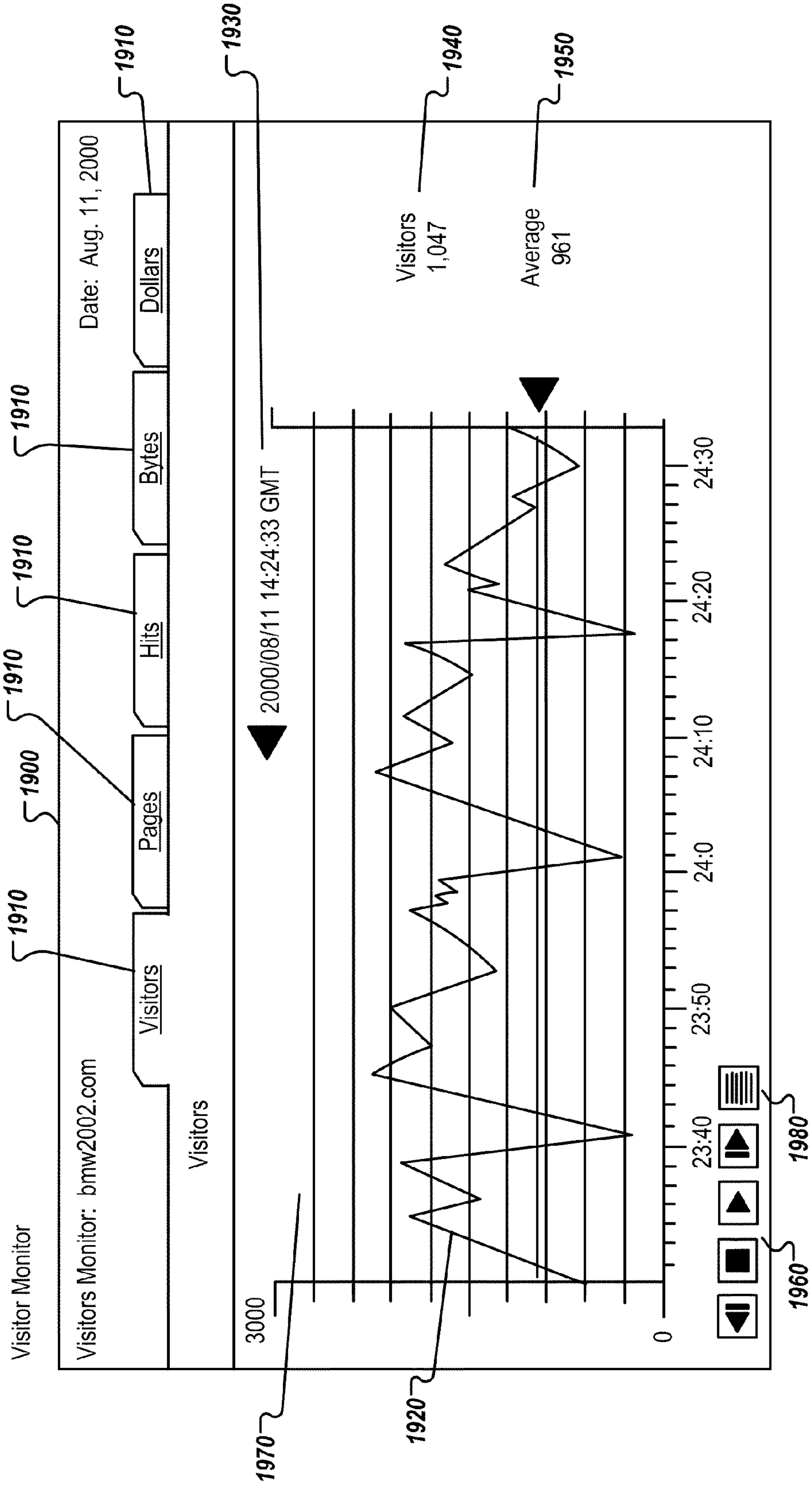
FIG. 22 is an example of a visitor monitor report created by the system of the present invention.

FIG. 22 illustrates an example of a visitor monitor report 1900 created by the system 100 of the present invention. The report 1900 preferably uses custom templates specifically designed for real-time reporting. The report 1900 is a web-based interface that provides a "live" real-time look at one of several possible data parameters 1910, such as visitors, pages, hits, bytes and dollars. The report preferably includes a visitor monitor graph 1920 that is preferably refreshed approximately every second to reflect new data. The data in the visitor monitor graph 1920 preferably moves from right to left as time progresses. The current time 1930 is preferably indicated above the visitor monitor graph 1920. In addition to the graphical display, the report 1900 preferably displays the current value 1940 of the data parameter 1910 currently being displayed, as well as the parameter's average value for that day 1950.

By monitoring the visitor data parameter 1910, the current traffic level can be monitored as it occurs. Controls 1960 are preferably provided that are configured so that the user can look at previous data, stop and freeze the graph, or continue with current data.

A small amount of Javascript is preferably used to control the refreshing of the visitor monitor report 1900. In addition, the visitor monitor report 1900 preferably uses a small amount of Javascript to time and reload the image 1970. The image 1970 is generated by the report engine 400, and uses the PNG format for compact lightweight operation. Since only the image 1970 is reloaded approximately every second, the visitor monitor report 1900 does not flicker when viewed with most browsers, thus creating an animated appearance to the graph 1920.

Temporal Visitor Drill Down

The images 1970 loaded into the visitor monitor report 1900 preferably include an HTML/javascript image map that provides "clickable" drill-down access to detailed information within the visitor monitor graph 1920. The visitor monitor report 1900 preferably contains a series of invisible rectangles (not shown) which cover the surface of the visitor monitor graph 1920. When the end-user clicks within the visitor monitor graph 1920, within one of the rectangles, that rectangle is mapped to a specific point in time. This time information is then compiled into a URL query and sent to the server to provide information on that specific point in time.

Figure 23:
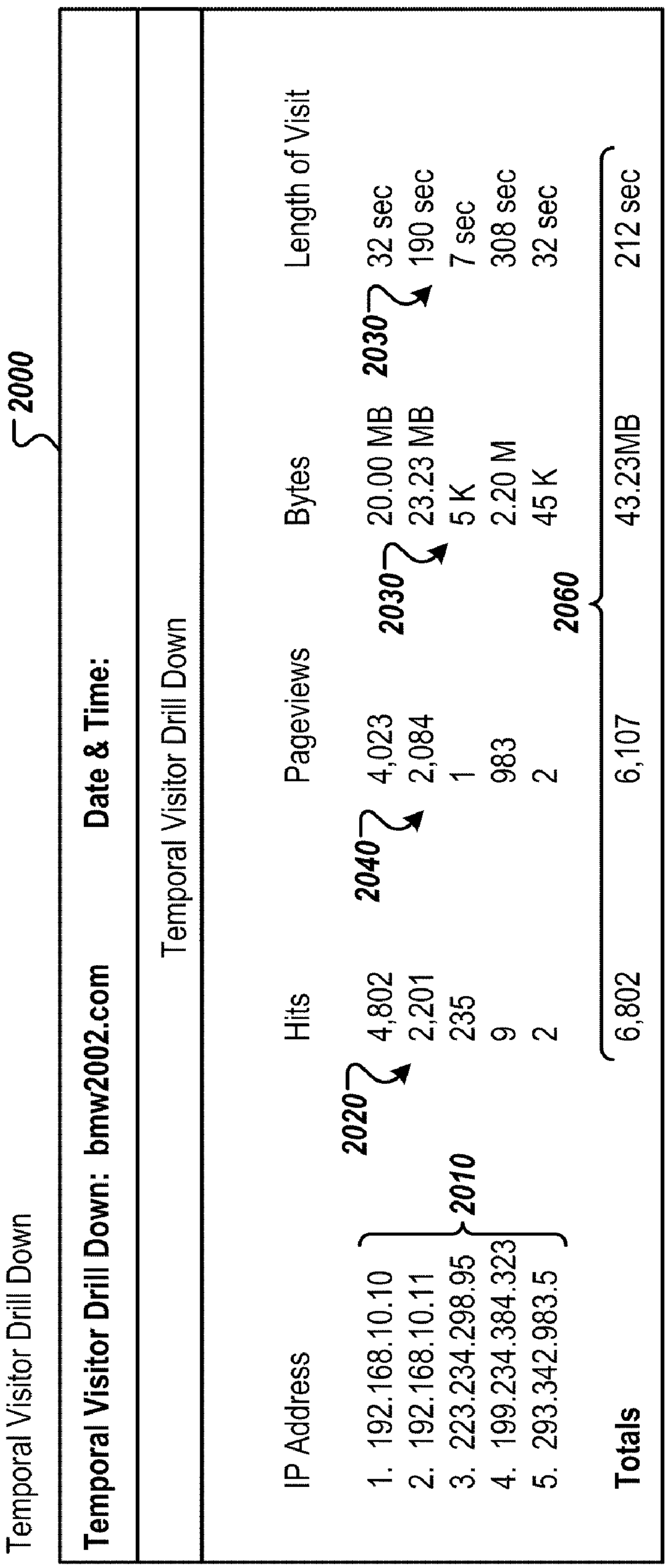
FIG. 23 is an example of a temporal visitor drill down report created by the system of the present invention.

FIG. 23 is an example of a temporal visitor drill down report 2000 created by the system 100 of the present invention, for displaying the time-specific data discussed above. All visitors 2010 that were currently active on the website at the selected time are listed by IP address and sorted based on the number of hits 2020. Bytes 2030, pageviews 2040, and length of visit 2050 are also preferably shown for each visitor 2010. The totals 2060 of bytes 2030, pageviews 2040, hits 2020 and length of visit 2050 for all visitors are also preferably displayed at the bottom of each column Administrators can use this drill down capability to quickly assess which visitors 2010 are responsible for the corresponding web server traffic. Hostile attacks from robots and web spiders can also be monitored in real-time. Administrators can take action against hostile clients by blocking their access to the servers.

Visitor Footprint

In addition to monitoring web server usage, the drill down capability described above is taken one step further. Each visitor 2010 listed in the Temporal Visitor Drill Down report 2000 is preferably selectable and linked to provide a visitor footprint on that specific visitor. All of the views are web-based and linking is preferably accomplished using simple HTML and Javascript. When the user selects a link on their browser, a new browser window opens and queries the report engine 400 for the specific information on that visitor.

FIG. 24 illustrates an example of a visitor footprint report 2100 created by the system 100 of the present invention. The visitor footprint report 2100 preferably contains detailed information on the activity of the selected visitor, including traffic information 2110, browser information 2120, referral information 2130, domain information 2140 and the visitor path 2150 (the specific path the visitor took through the web site).

If the visitor shown in the visitor footprint report 2100 is responsible for an e-commerce transaction that is processed by the system 100, then additional e-commerce information 2160 is preferably shown in the visitor footprint report 2100. If the visitor shown in the visitor footprint report 2100 looked at multimedia clips that are captured by the system 100, then additional streaming information 2170 is preferably shown in the visitor footprint report.

The browser information 2120 is preferably analyzed to see if it matches a known browser or platform. If the browser is recognized then an icon of the browser and platform 2180 can be optionally shown as part of the browser information 2120. If the visitor is identified as a robot, then an icon of a robot (not shown) can be optionally shown as part of the browser information 2120. This can be useful for quickly identifying hostile attacks from aggressive robots and spiders which can flood the web servers 500 with requests, creating a slow down in response times.

The visitor footprint report 2100 can provide insight into the usage of the website as well as help analyze specific visitors. While the detailed activity of the visitor can be monitored, the system 100 preferably does not record, use, or display any personal or identification information such as e-mail addresses, names, etc. Each visitor, while specific in the database 300, preferably remains anonymous.

System Meter

Figure 25:
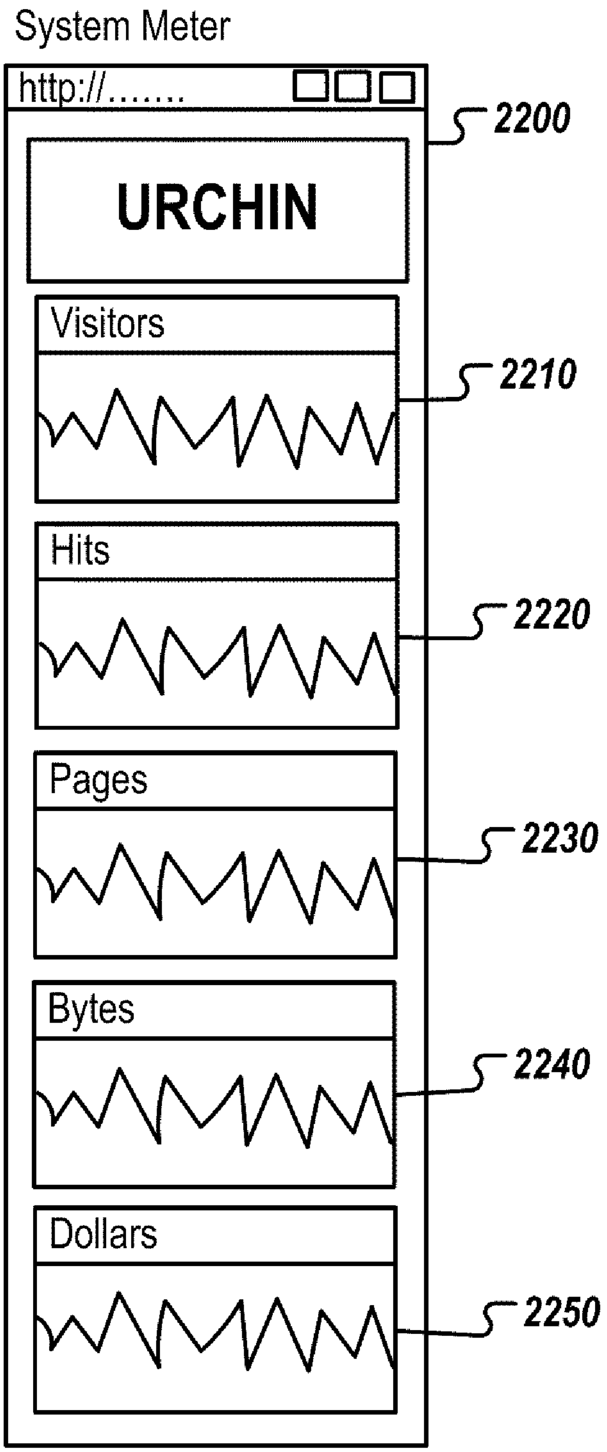
FIG. 25 illustrates an example of a system meter report created by the system of the present invention.

FIG. 25 illustrates an example of a system meter report 2200 created by the system 100 of the present invention. The system meter report 2200 is similar to the web-based visitor monitor report 1900 shown in FIG. 22. However, instead of providing a full-sized analysis tool, the system meter report 2200 is designed to be small enough to fit on a desktop computer screen at all times.

The system meter report 2200 contains multiple thumbnail sized report images (2210, 2220, 2230, 2240, 2250) that all refresh in the same manner as the visitor monitor report 1900. To access the system meter report 2200, the end-user preferably selects a collapse button 1980 (shown in FIG. 22) or a "system meter" navigation button (not shown) within the visitor monitor report 1900. When the system meter report 2200 is requested from the visitor monitor report 1900, the window containing the visitor monitor report 1900 preferably closes and a new smaller window appears on the desktop computer screen containing the system meter report 2200.

The system meter report 2200 is preferably configured so that a user can resize the system meter report 2200 (with, for example, a computer mouse) creating a compact live web-meter that gives them constant monitoring of critical systems. The system meter report 2200 is also preferably configured so that selecting one of the report images (2210, 2220, 2230, 2240, 2250) re-opens the full-sized visitor monitor report 1900.

The system meter report 2200 preferably displays graphs of visitors 2210, hits 2220, pages 2230, bytes sent 2240, and money 2250 (if e-commerce is activated).

E-Commerce Reporting

As businesses move from providing passive information about their products to providing interactive shopping capabilities, successful analysis of internet traffic can provide valuable information for making strategic business decisions.

In one preferred embodiment of the present invention, Return On Investment Reporting (ROIR) technology is used to provide the ability to report on internet traffic in terms of revenue. All aspects of the visitor reporting are correlated to dollars spent on the website, providing detailed analysis of when and where revenue is generated. Marketing and advertising managers can use this information to track the effectiveness of banner ads, the location of and behavior of shoppers and more.

The key to this technology is the present invention's ability to correlate data in a Visitor-Centric way. The Visitor-Centric configuration of the present invention allows the system 100 to report on dollars spent in correlation with any visitor parameter.

E-commerce websites use shopping cart software (hereinafter "shopping carts") to provide a secure method for on-line ordering. Shopping carts allow the end-user to add products to their virtual shopping basket, change quantities and check out, similar to a normal shopping experience. There are many commercial shopping cart products such as Miva's Merchant™ and Mercantec's Softcart™.

Whether an e-commerce site uses an off-the-shelf product or a custom engineered application, the concept is the same. The shopping cart software keeps track of each visitor shopping session. As products are added to an individual's shopping cart, the software updates the visitor's specific information. When the visitor decides to check out and purchase the products, the shopping cart provides the necessary shipping and billing forms and can process the transaction.

E-Commerce Log File Format

The internet traffic monitoring and analysis system and method of the present invention utilizes the e-commerce log files 580 produced by the shopping carts to perform the e-commerce data correlation. However, the log file formats used by different shopping carts can vary. A preferred e-commerce log file format for use with the internet traffic monitoring and analysis system and method of the present invention is described below.

The e-commerce log file format is preferably a tab-separated, multiline format. The transaction preferably begins with the exclamation mark (!) character (which is thusly prohibited from the rest of the data). The first line of the e-commerce log file preferably contains the geographic and overall information on the e-commerce transaction. Subsequent lines preferably contain details on individual products. The preferred basic format of the e-commerce log file 580 is as follows:

```
!transfield1 transfield2 . . .
productfield1 productfield2 . . .
productfield1 productfield2 . . .
.
.
.
!transfield transfield2 . . .
etc.
```

Blank fields preferably contain a dash (-) character. The preferred format for the transaction line is as follows:

\!% {ORDERID}% h %{STORE}%{SESSIONID}% t %{TOTAL}%{TAX}% {SHI PPING}%{BILL_ CITY}%{BILL_STATE}%{BILL_ZIP}%{BILL_CNTRY}

| | | |
|---|---|---|
| where | %{ORDERID} | is the order number. |
| | %h | is the remote host (see apache.org). |
| | %{STORE} | is the name/id of the storefront. |
| | %{SESSIONID} | is the unique session identifier of the customer. |
| | %t | is time in the common log format |
| | %{TOTAL} | is the transaction total including tax and shipping. (decimal only, no "$" signs). |
| | %{TAX} | is the amount of tax charged to the subtotal. |
| | %{SHIPPING} | is the amount of shipping charges. |
| | %{BILL_CITY} | is the billing city of the customer. |
| | %{BILL_STATE} | is the billing state of the customer. |
| | %{BILL_ZIP} | is the billing zip of the customer. |
| | %{BILL_CNTRY} | is the billing country of the customer |

The preferred format for the product line is:

%{ORDERID}%{PRODUCTCODE}%{PRODUCTNAME}% {VARIATION}%{PRICE}%{QUANTITY}%{UPSOLD}

| | | |
|---|---|---|
| where | %{ORDERID} | is the order number. |
| | %{PRODUCTCODE} | is the identifier of the product. |
| | | is the name of the product. |
| | % {VARIATION} | is an optional variation of the product for colors, sizes, etc. |
| | %{PRICE} | is the unit price of the product (decimal only, no "$" signs). |
| | %{QUANTITY} | is the quantity ordered of the product. |
| | %{UPSOLD} | is a boolean (1\|0) if the product was on sale. |

An aspect of the present invention is the optional provision of a plug-in module for existing shopping carts that will allow the shopping cart to create the e-commerce file log 580 in the preferred format.

E-Commerce Visitor Correlation

In order to provide the ROIR reporting described above, the system 100 performs a special correlation between the e-commerce transaction data in the e-commerce log file 580 and normal website visitor traffic data in the standard log files 510.

As discussed above, both the standard log files 510 and the e-commerce log files 580 are processed by the log engine 200. As discussed above in connection with FIGS. 3-9, each line of the log files 510 and 580 is processed and passes through the following steps. (1) the log line 512 of the log file 510 or 580 is read into the database buffer 250; depending on the format of the log file, the log line 512 is processed and identified; (3) the website identification module is used if multiple websites are logged into the same log file 510 or 580; (4) the visitor identification module uses the IP number and a timestamp found in the log line 512 (or session id) to establish the unique identity of the visitor; (5) the visitor ID is used to determine the record number in the visitor table 310'; and (6) the record is updated with the information from the log line 512.

Figure 26:
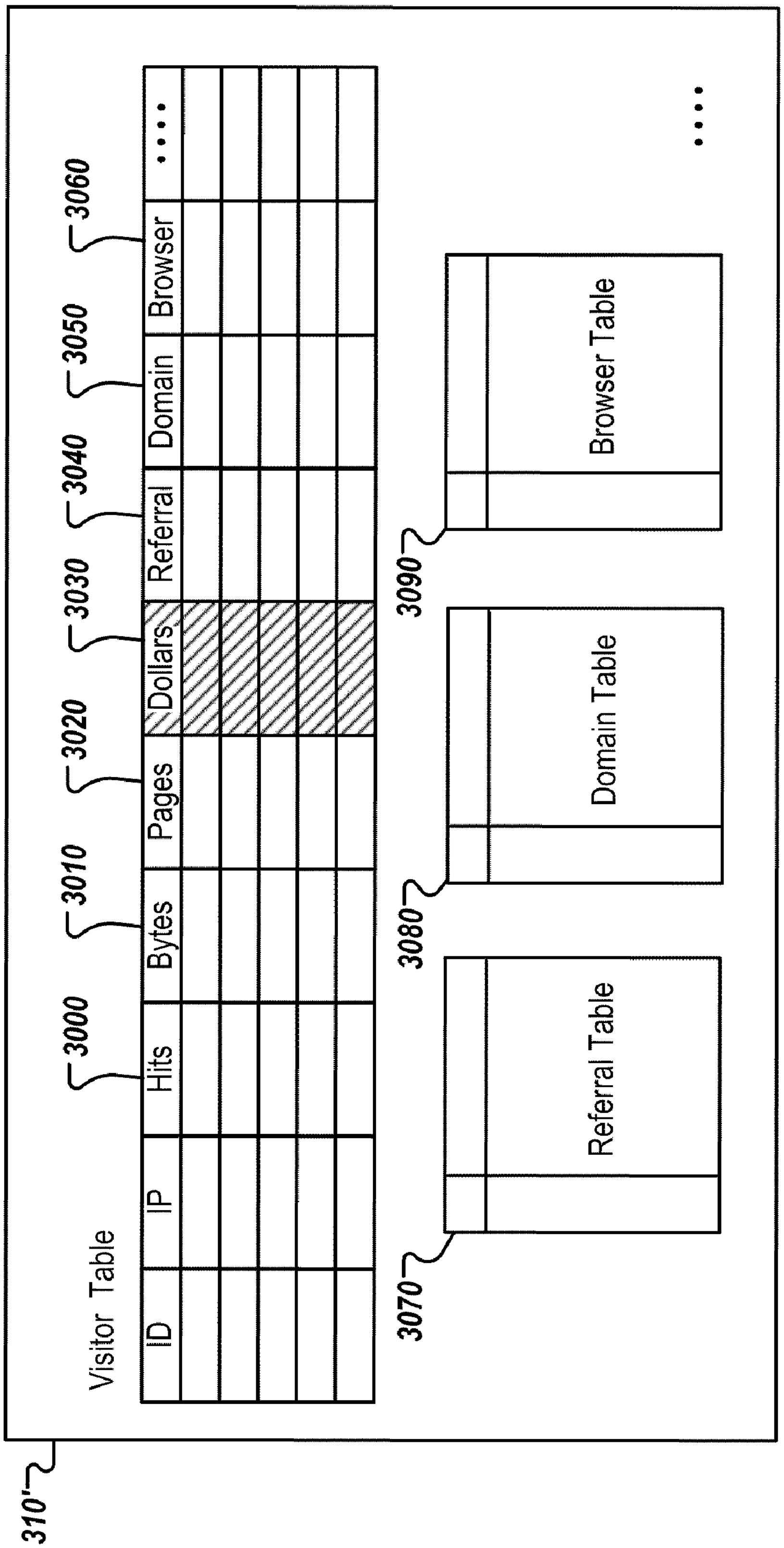
FIG. 26 shows visitor table containing e-commerce data, and residing in the database buffer.

FIG. 26 shows the visitor table 310' in the database buffer 250. As discussed above, the visitor table 310' may include many fields, such as Hits 3000, Bytes 3010, Pages 3020, Dollars 3030, Referrals 3040, Domain 3050, Browser 3060, etc. The visitor table 310' is where the e-commerce correlation is done.

The e-commerce log file 580 will update the visitor's Dollars field 3030, which indicates money spent by the visitor. The remaining fields are updated using the standard log file 510. The Dollars field 3030 is used to determine money spent on the website in terms of the other fields (parameters).

For example, the Referral field 3040 in the visitor table 310' holds a record number to an entry in the referral data table 3070. The referral in the referral data table 3070 indicates how the visitor found the website. For example, if the visitor came from the yahoo.com™ website, then the referral field 3040 in the visitor table 310' would hold the record number pertaining to the yahoo.com™ entry in the referral data table 3070. All visitors that came from yahoo.com™ would have the same referral record number in the referral field 3040. Similarly, the Domain and browser fields 3050 and 3060 in the visitor table 310' would hold record numbers to entries in the domain data table 3080 and browser data table 3090. The other fields 3000, 3010 and 3020 would likewise have data tables associated with them (not shown).

By looping over the visitor table 310', a money amount can be associated with each entry in any of the data tables. If, for example, a money amount is associated with each entry in the referral data table 3070, all shoppers that came from yahoo.com™ (as an example) would be aggregated to produce a return-on-investment indicator.

Figure 27:
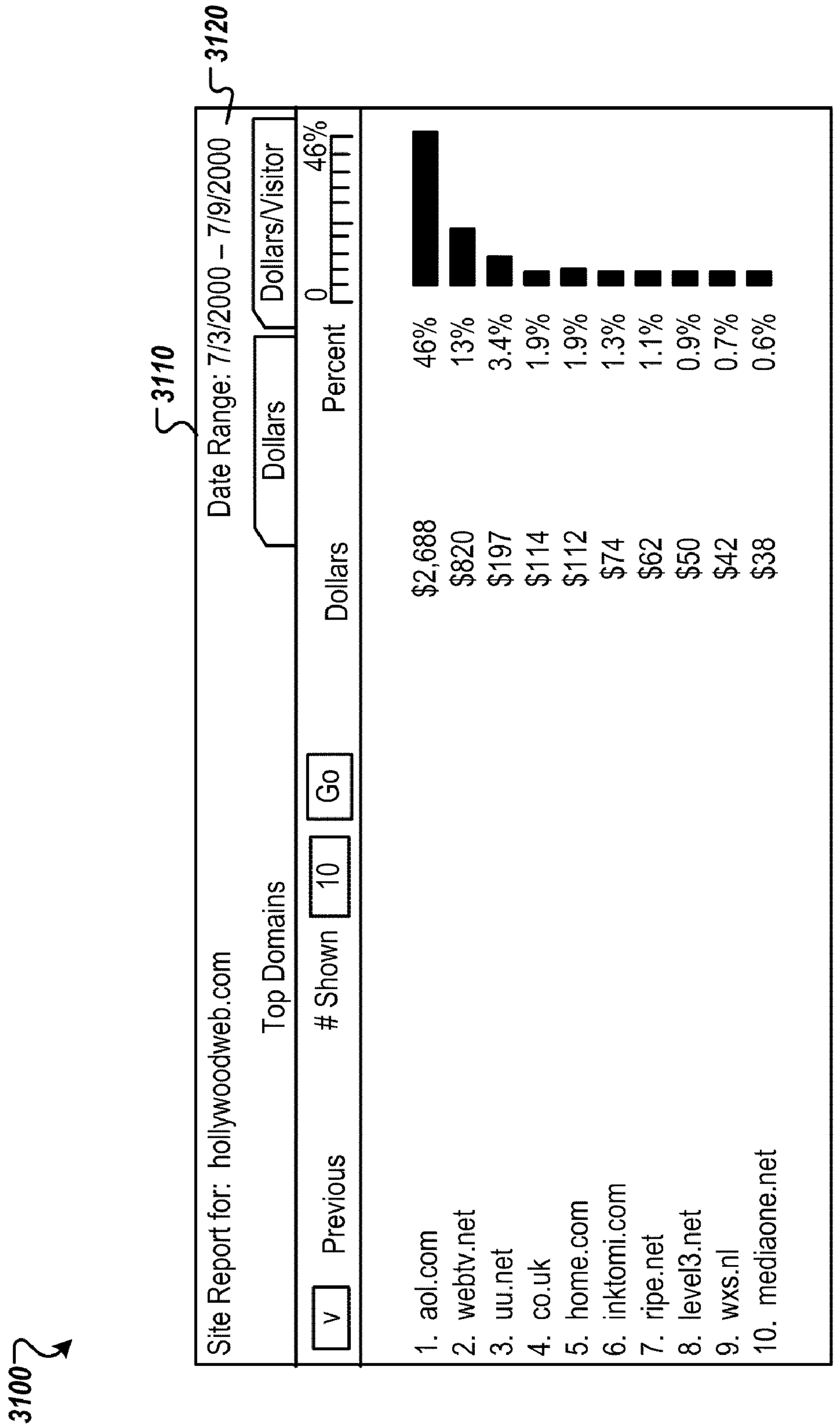
FIG. 27 shows an example of an ROIR e-commerce report generated by the system of the present invention.

FIG. 27 shows an example of an ROIR e-commerce report generated by the system 100 of the present invention. The report 3100 uses the domain data table 3080, shown in FIG. 22, to produce a top-10 report of Internet Domains whose visitors spent the most money on the website represented by the report 3100. In the example report 3100, Aol.com™ is the top domain in terms of money, spending approximately 46% of all money spent on the website.

The total money spent by all the visitors for each domain is displayed when the "Dollars" tab 3110 is selected. The average amount of money spent by each visitor at each domain can also be displayed selecting the "Dollars/Visitor" tab 3120. The average amount of money spent by each visitor is calculated by dividing the total amount of money spent at each domain by the number of visitors to the domain.

E-commerce website owners can use these correlations to make valuable business decisions. The system and method of the present invention can correlate money to keywords, banner ads, search engines, referrals, domains, countries, browsers, platforms, or any other parameter of interest. The website operators can monitor the performance of search engine registrations, banner ad placements, regional ad campaigns, and more.

User Interfaces/System Reports

Examples of preferred user interfaces and system reports will know be discussed. All reports and interfaces are preferably web-based and viewed with a web browser. While not all possible reports are shown, the reports shown are representative of the types of reports and report configurations that are possible with the system and method of the present invention. Accordingly, it should be appreciated that the configuration and types of reports, as well as the configuration and types of user interfaces may vary from those shown while still falling within the scope of the present invention.

Further the user interfaces described below are for generation of static reports. The user interfaces used for real-time reports were described above in connection with FIGS. 22-25.

Figure 28:
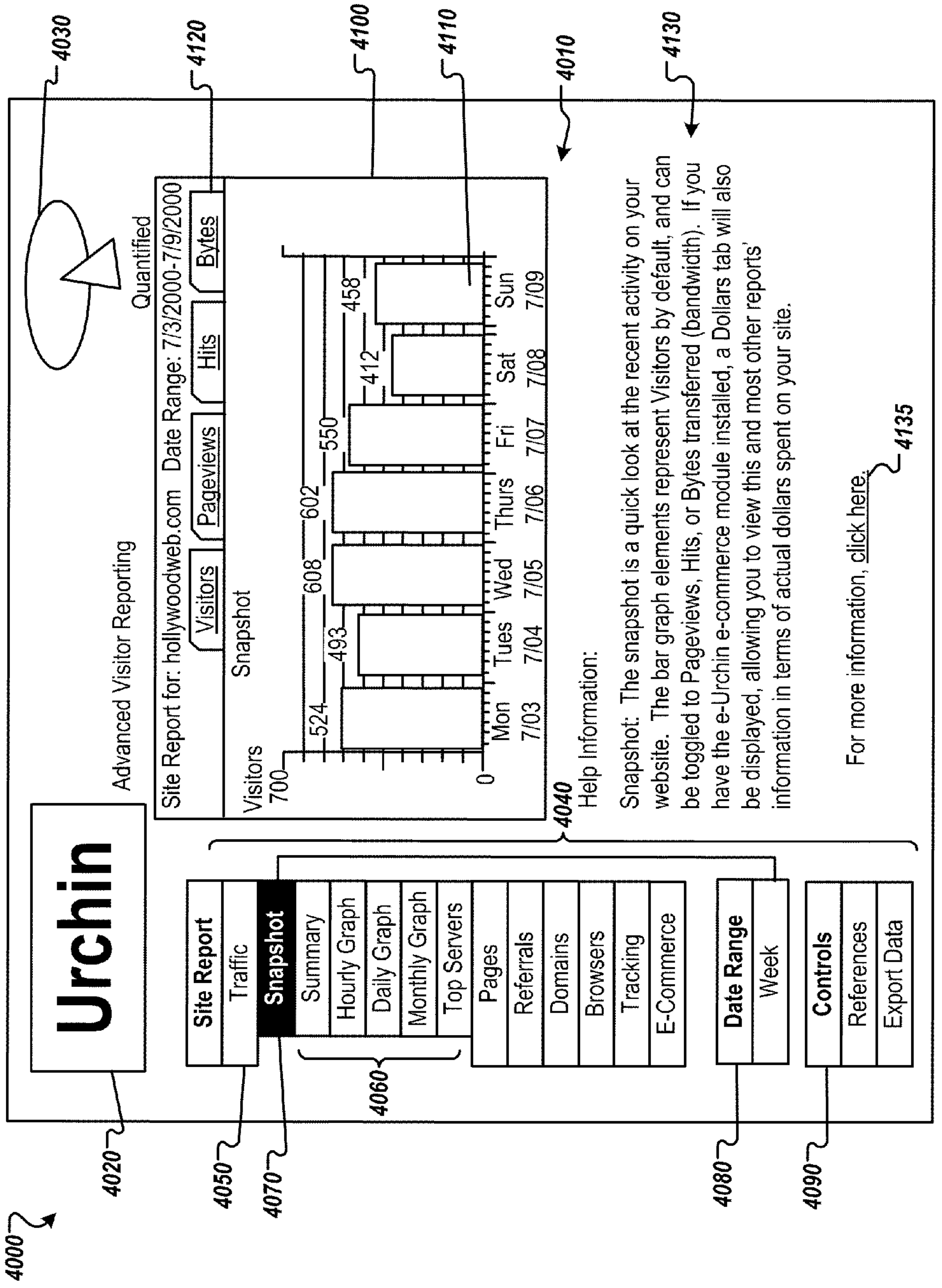
FIG. 28 shows an example of a snapshot report generated by the system of the present invention.

FIG. 28 shows a preferred browser-based user interface 4000. This is preferably the first user interface 4000 shown when the user first accesses the reporting interface of the system 100. The user interface 4000, preferably contains areas 4020 and 4030 for displaying product and/or company logos. The user interface 4000 also includes a main reporting window 4100 for displaying a currently chosen report.

The user interface 4000 preferably includes a navigation area 4040 that contains a collection of menus that group the available reports into different categories, preferably seven main categories, each with an associated link 4050: Traffic; Pages; Referrals; Domains; Browsers; Tracking; and E-Commerce. A collection of links to specific reports 4060 related to a chosen category link 4050 is preferably displayed under a chosen category link 4050. The currently chosen report link 4070 is preferably indicated by a change in color or shading. In the example shown in FIG. 28, the currently chosen report link 4070 corresponds to the "Snapshot" report.

The user interface 4000 preferably includes a "date range" functions area 4080. Depending on the report chosen, this date range functions area 4080 allows the user to select the date range of the report being shown. The user interface also preferably includes a controls area 4090 that preferably includes preferences and report exporting features. The preferences function of the controls area 4090 allows the user to change report settings, such as the language that is used for display. The exporting function of the controls area 4090 allows the user to export the currently viewed data for use in other applications, such as Microsoft Excel™.

The user interface 4000 also preferably includes a Help Information area 4130, which gives a brief synopsis of the report being displayed and provides a link 4135 for more in-depth information.

Traffic Related Reports

The Snapshot report 4010 shown in FIG. 28 is preferably a bar graph 4110 of the last 7 days of web site traffic in terms of various fields, preferably Visitors, Pageviews, Hits, or Bytes. There are preferably tab controls 4120 on the report 4010 that allow the user to select which field is displayed. The date of each day is preferably shown below the bars in the graph 4110.

Figure 29:
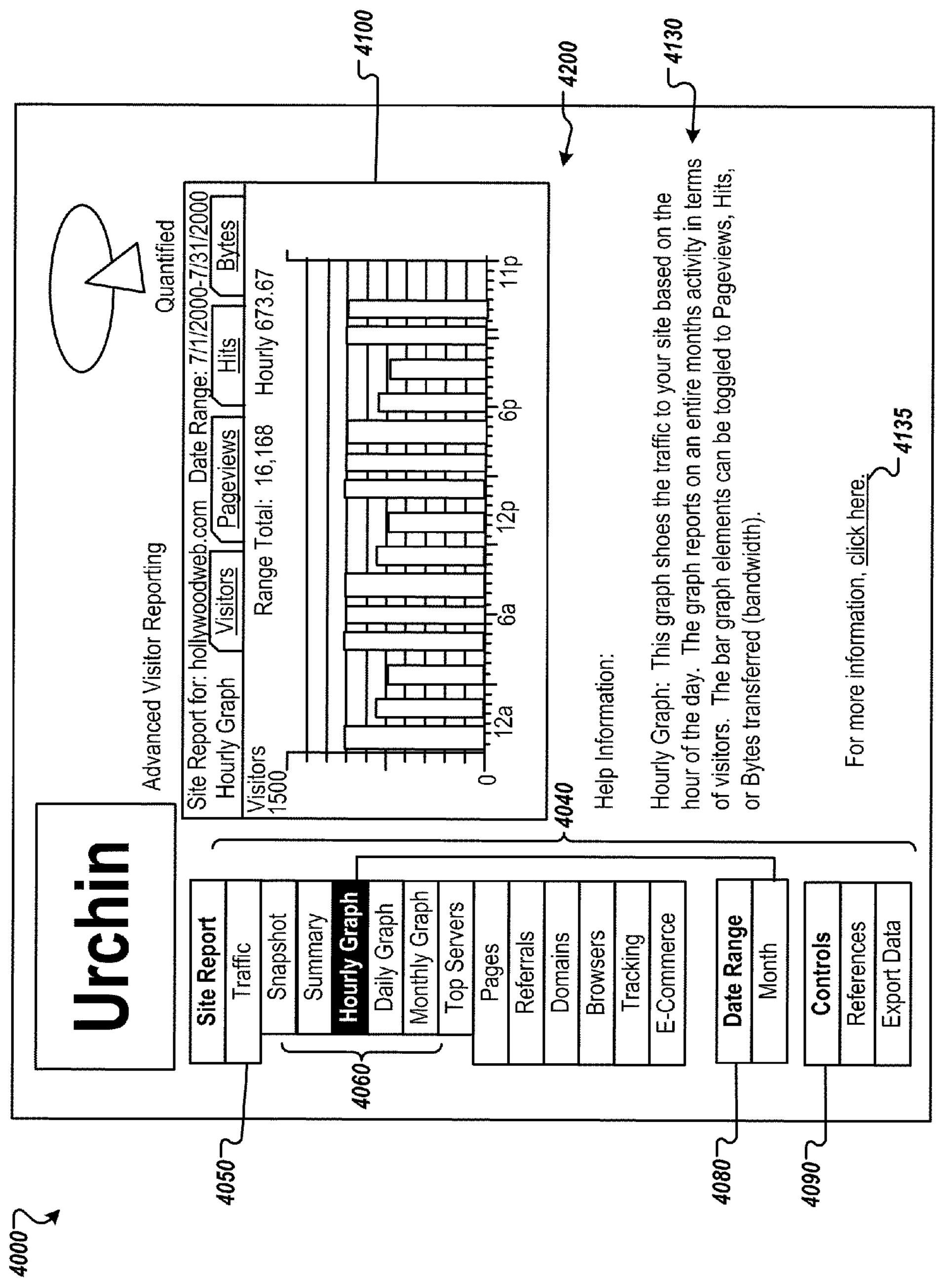
FIG. 29 shows an example of a user interface and an hourly graph report generated by the system of the present invention.

FIG. 29 shows an example of an Hourly Graph report 4200. The Hourly Graph report preferably shows traffic versus hour of the day in terms of various fields, preferably Visitors, Pageviews, Hits, or Bytes. There are preferably tab controls 4120 on the report 4200 that allow the user to select which field is displayed.

The Hourly Graph report 4200 is preferably a bar graph indicating the 24 hours of the day from left to right. This report allows administrators to see when peak activity is expected and when to plan site maintenance and upgrades.

Other reports available under the Traffic category preferably include the Summary, Daily Graph, Monthly Graph and Top Servers reports. The Summary report gives a text based summary of overall traffic to the site. The Daily Graph is similar to the Hourly Graph report 4200, except that the traffic is displayed as a function of the day of the month. The Monthly Graph report provides traffic displayed versus month of the year, and the Top Servers report indicates which log files or servers are responsible for the most traffic in the cluster.

Pages Related Reports

Figure 30:
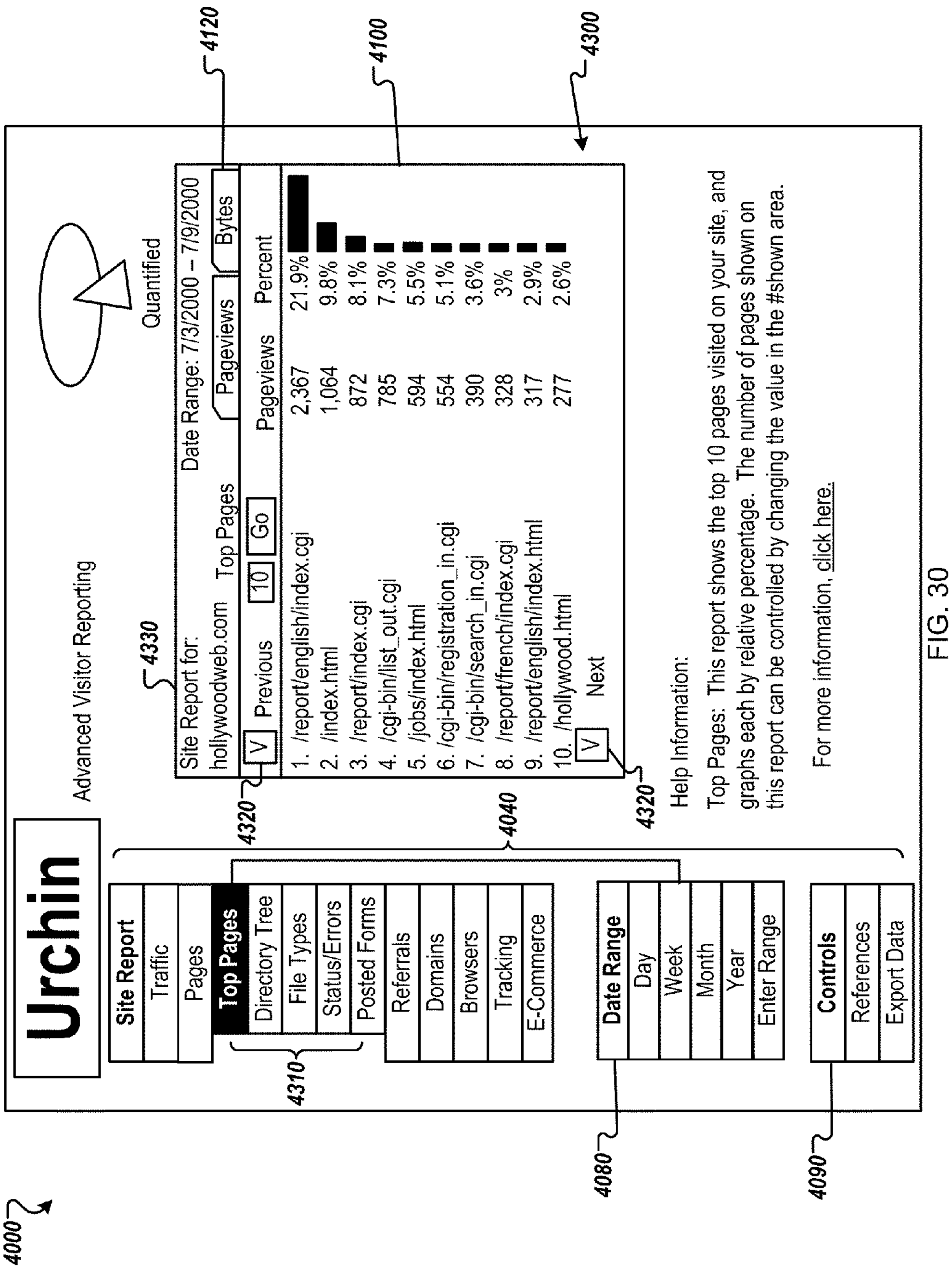
FIG. 30 shows an example of a top pages report generated by the system of the present invention.

FIG. 30 shows an example of a Top Pages report 4300. The Top Pages report 4300 is one of the reports listed under the Pages menu 4310. The Top Pages report 4300 preferably indicates a top-ten type list, ranking which pages in the website are the most visited. The tabs 4120 are preferably used to view the report 4300 in terms of either Pageviews or Bytes transferred. Next and previous buttons 4320 are preferably provided that allow the user to scroll through the Top Pages Report 4300. The number of entries shown are preferably adjusted with the #Shown menu 4330.

Figure 31:
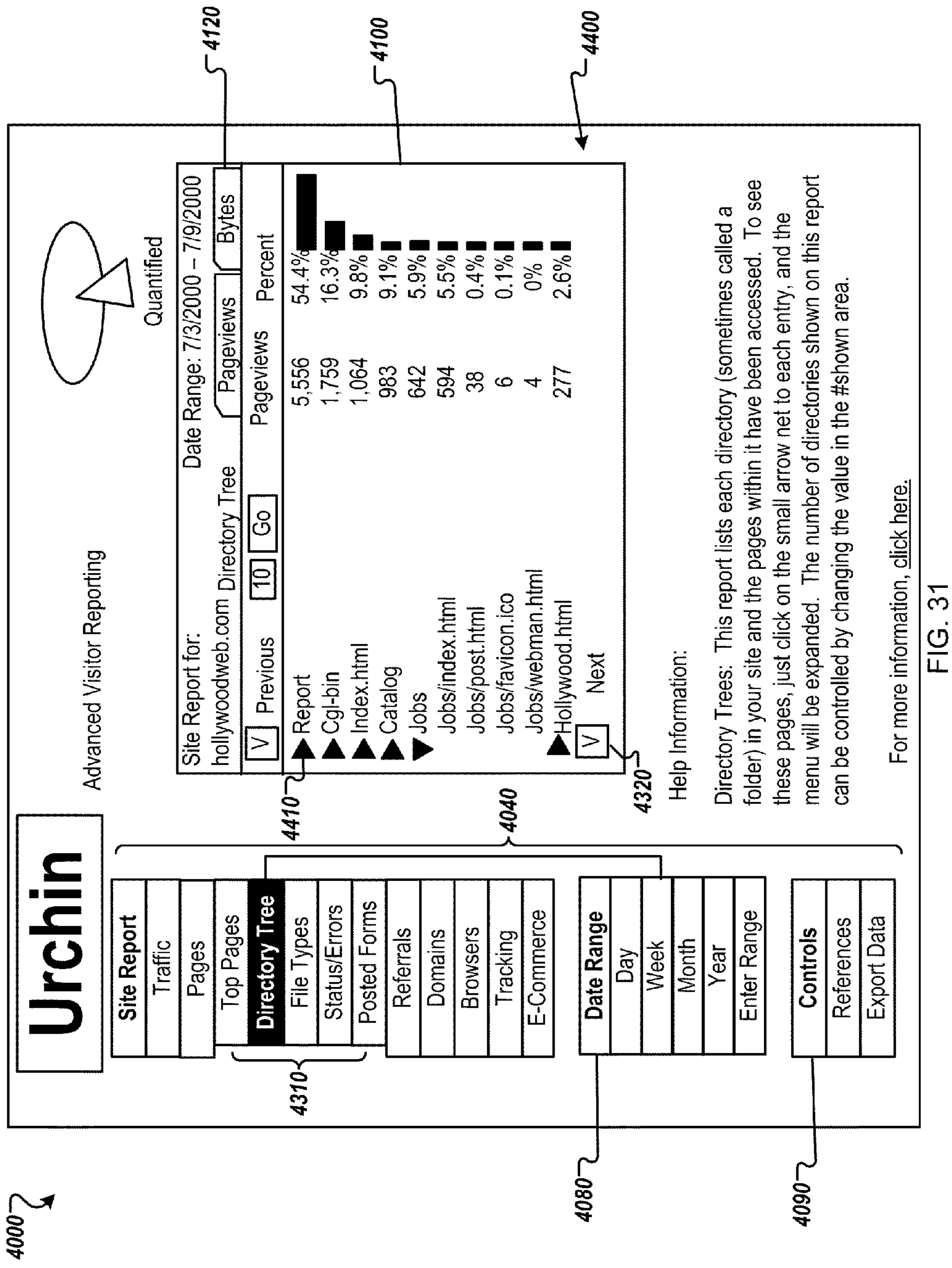
FIG. 31 shows an example of a directory tree report generated by the system of the present invention.

FIG. 31 shows an example of a Directory Tree Report 4400. The Directory Tree Report 4400 is similar to the top pages report 4300 of FIG. 30, except that the Directory Tree Report 4400 preferably includes links 4410 next to each entry that can be selected to open information below that entry. This allows for easy display and navigation of hierarchical type data, such as a directory structure.

The directory tree report 4400 indicates which directories within the website architecture are being accessed the most. Under each directory, the end user can drill down to see the subdirectories or individual pages contained within the primary directory by selecting the links 4410.

Other pages-related reports in the Pages menu 4310 preferably include File Types, Status/Errors, and Posted Forms. The File Types report is a top-ten type report that indicates which file extensions or types are accessed the most. This allows the user to distinguish between HTML page, GIF images, etc. The Status/Errors report is a tree-type report that indicates status codes and error messages that occur during web content delivery. The Posted Forms report is a top-ten type report that indicates the forms that were submitted using the POST method as defined in the HTTP protocol.

Referrals Related Reports

Figure 32:
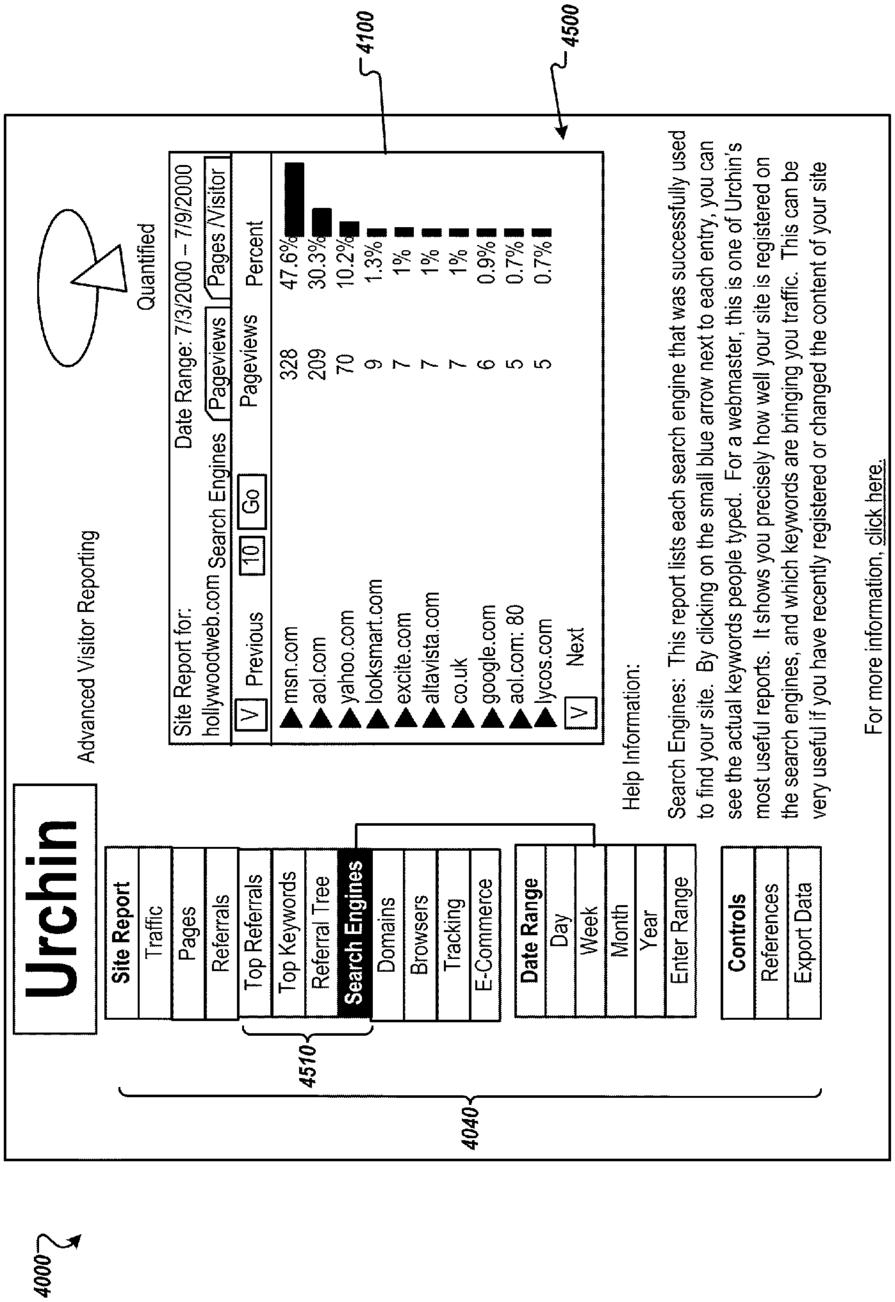
FIG. 32 shows an example of a search engines report generated by the system of the present invention.

FIG. 32 shows an example of a Search Engine report 4500 from the Referrals menu 4510 of the navigation area 4040. The Referrals menu 4510 provides reports related to how the visitor found a website.

The Search Engines report 4500 contains a tree-type list of the most used search engines. Each search engine can then be expanded to see which keywords were used during those searches.

Additional reports in the Referrals menu 4510 preferably include Top Referrals, Top Keywords, and the Referral Tree. The Top Referrals reports is a simple top-ten type list of the top referring URLs. The Keywords report indicates the top keywords used across all search engines. The Referral Tree report breaks down the Referral URLs by domain.

Domains Related Report

Figure 33:
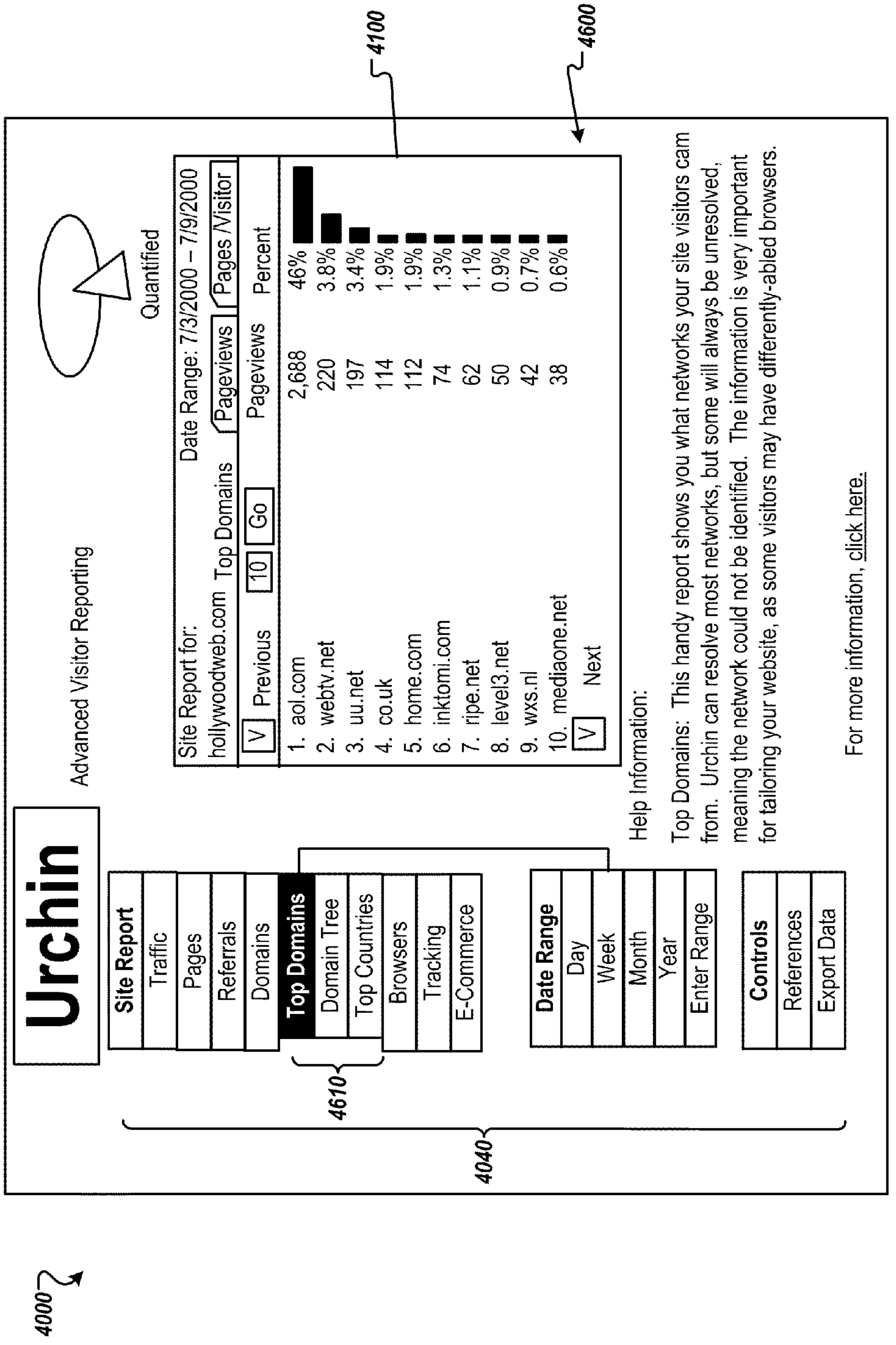
FIG. 33 shows an example of a top domains report generated by the system of the present invention.

FIG. 33 is an example of a Top Domains report 4600, which indicates regional and network information about the visitors. The visitor's domain is determined by the IP address of the visitor. The domain is resolved using the Reverse DNS module 260 within the log engine 200 described previously.

Additional reports under the Domains menu 4610 in the navigation area 4040 preferably include Domain Tree and Top Countries. The Domain Tree report provides the different levels of domains. Primary domains such as .com and .edu are shown first. Preferably, these can be expanded to show detailed information within. The Top Countries report expands and analyzes which countries people are coming from.

Browsers Related Reports

Figure 34:
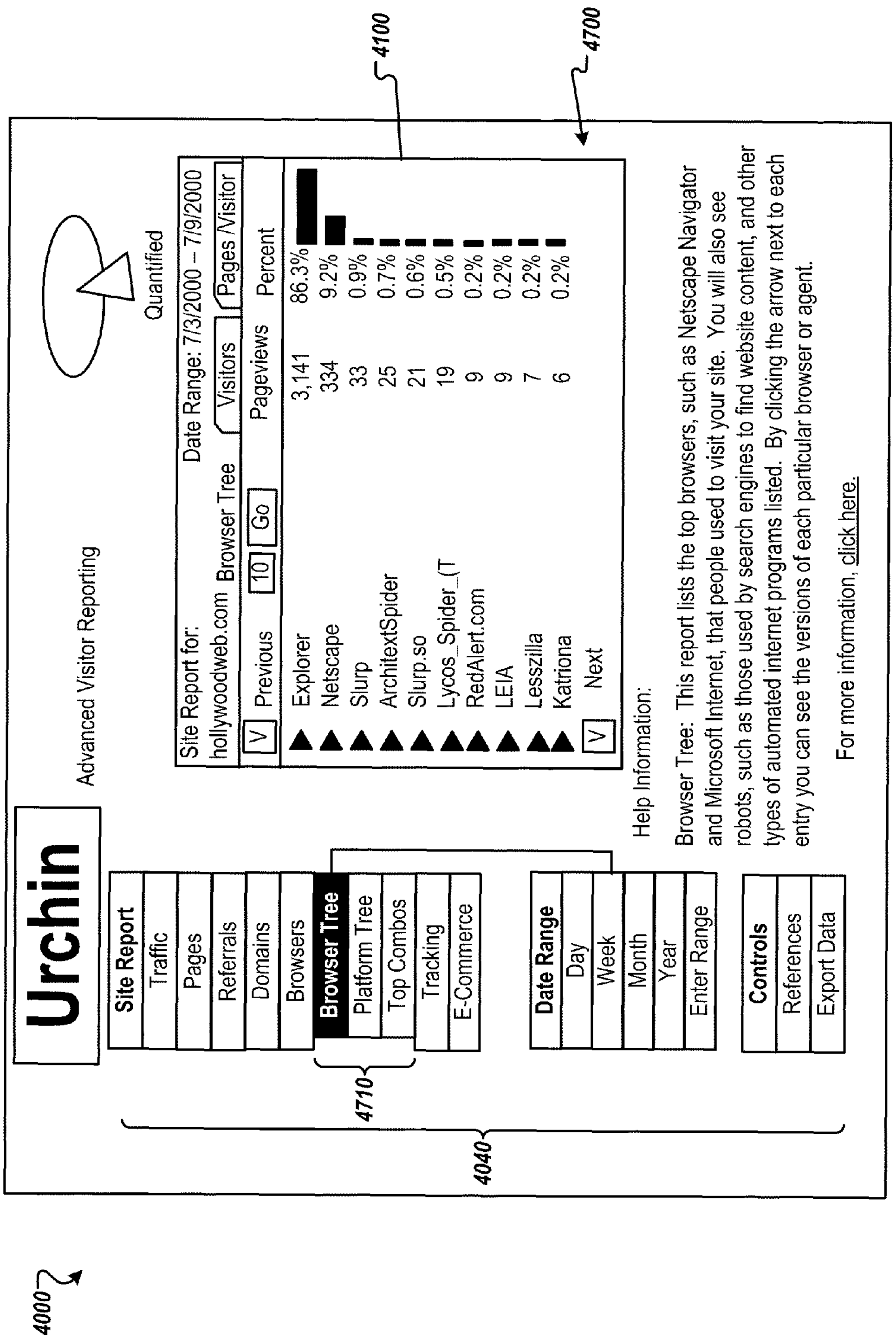
FIG. 34 shows an example of a browser tree report generated by the system of the present invention.

FIG. 34 shows an example of a Browser Tree report 4700, which is a tree-type report that ranks the most widely used browsers by visitor to the website. Browsers such as Internet Explorer™ and Netscape™ are reported upon as a whole and by version. Each primary browser can be expanded to see the breakdown by version.

Additional reports in the Browsers menu 4710 of the navigation area 4040 preferably include Platform Tree and Top Combos. The Platform Tree report indicates the operating system of the visitor. It is a tree-type report that can be expanded to show the versions under each platform. The Top Combos report ranks the correlation between browser and platform.

Tracking Related Reports

Figure 35:
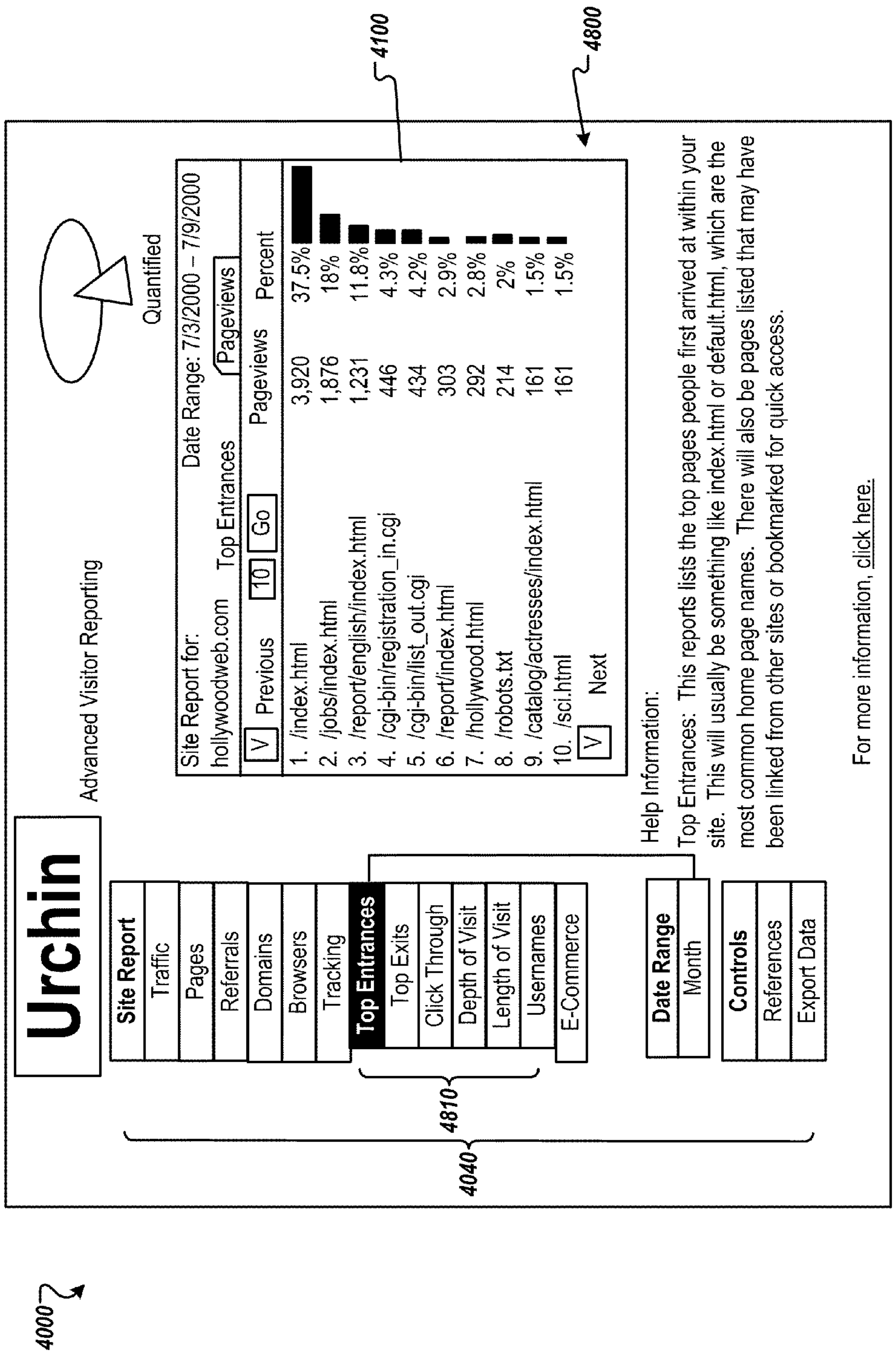
FIG. 35 shows an example of a top entrances report generated by the system of the present invention.

FIG. 35 shows an example of a Top Entrances report 4800. As part of the Tracking menu 4810 within the navigation area 4040, the Top Entrances report 4800 indicates the starting point of visitors in the website. Additional reports in the Tracking section 4810 preferably include Top Exits, Click Through, Depth of Visit, Length of Visit, and Usernames.

The Top Exits report provides a list of the last page visitors looked at before leaving the site. The Click Through report indicates the click percentage from any one page to another. The Depth of visit report provides a histogram of the number of pages viewed by visitors. The Length of Visit report provides a histogram of the time spent on the site by visitors. The Usernames report analyzes the usage of password protected areas of a website by listing the usernames that were used to login to the those sections.

E-Commerce Related Reports

Figure 36:
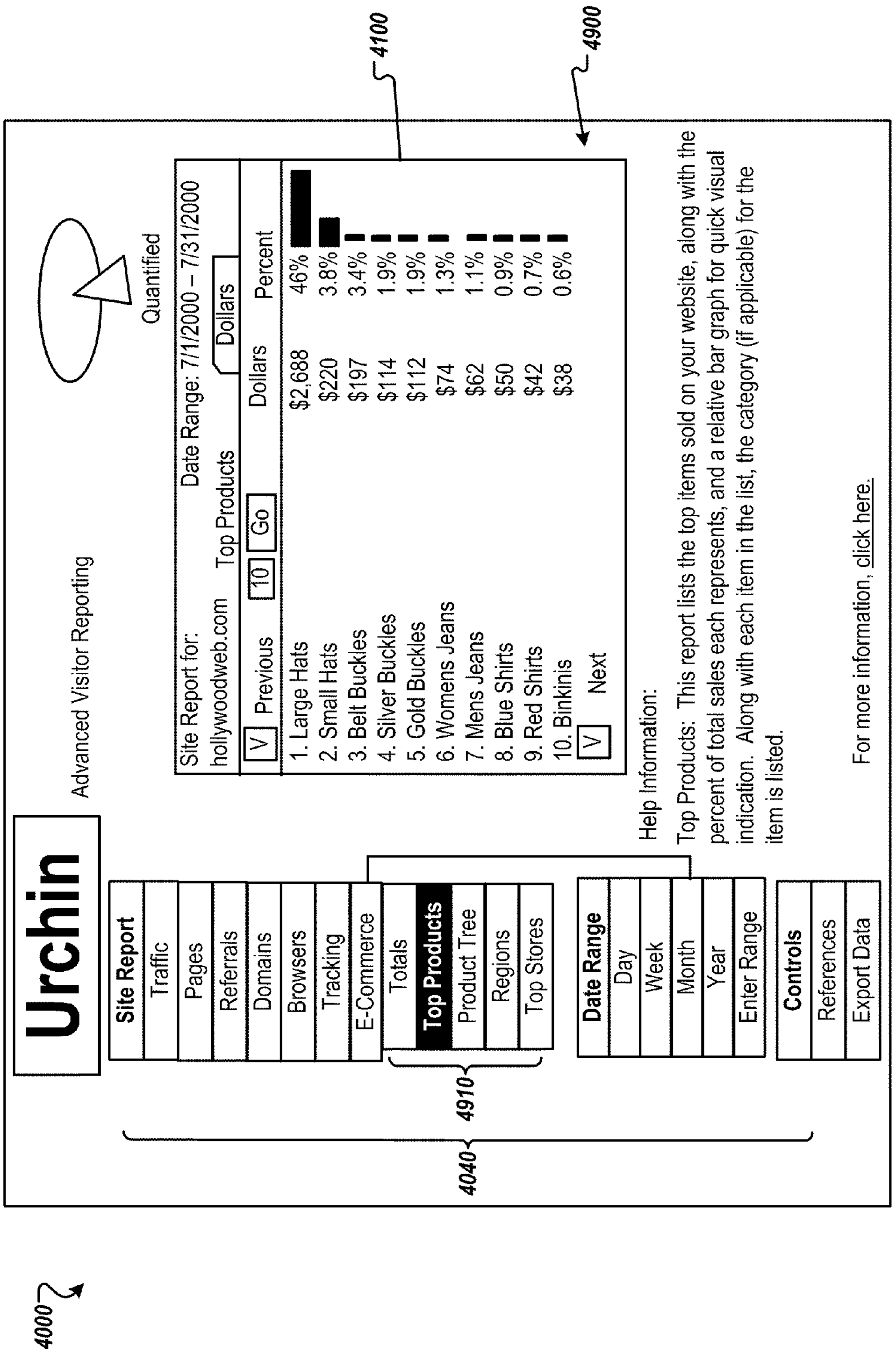
FIG. 36 shows an example of a top products report generated by the system of the present invention.

FIG. 36 shows an example of a Top Products report 4900, which is part of the E-Commerce menu 4910 in the navigation area 4040. The Top Products report 4900 indicates the Top Products purchased from the site by revenue. Additional reports in the E-Commerce menu 4910 preferably include Totals, Product Tree, Regions, and Top Stores. The Totals report gives a summary of overall e-commerce activity. The Product Tree report groups products by category. The Regions report indicates the regional location of shoppers including cities, states and countries. If multiple store fronts are used by the same shopping system, the Top Stores report can breakdown revenue by storefront.

System Integration

The system and method of the present invention can be configured in many different ways. From single server configurations to complex load balancing systems, the system and method of the present invention is flexible in its integration abilities. While it is difficult to catalog every possible architecture, several possible configurations are described below.

Webserver vs. Dedicated Server

The system and method of the present invention can be implemented directly on the web server 500 that produces the log files (510, 580), or on a separate dedicated computer. If the system 100 is implemented directly on the web server 500, it can then use the web server 500 for the reporting web server 520. If the system 100 is implemented on a dedicated box, then a web server 520 will need to be configured on the dedicated computer in order to service the report requests.

Access to log files is slightly more complicated on a dedicated computer. If the system 100 is implemented on a dedicated computer, then the log files (510, 580) from the web server 500 will need to be accessible to the dedicated computer by using FTP, NFS, or some other suitable disk access method. Real-time processing of log files requires writing permission to the log files (510, 580) which may require an extra configuration step if using a dedicated computer.

As long as the log files (510, 580) are accessible (with permissions) and a web server is available, the system 100 can work just as well directly on the web server 500 or on a dedicated computer.

One Website vs. Multiple Websites

The system and method of the present invention can handle multiple websites. During integration, a unique reporting directory for data storage can be configured for each of the websites. The system 100 will link the individual report directories back to the main installation, so that there is only one copy of the templates and icons. Users will need internet access to the reporting directories. Thus, the web server 520 configuration should be similar to the system 100 configuration. A typical installation will use a subdirectory within each website's document root to store and access the reports.

Whether there is one website or many, the integration preferably provides a unique web accessible directory for each website configuration.

Distributed Logs vs. Central Logs

Web servers 500 can be configured to create unique log files (510, 580) for each website in the web server's configuration, or a single log file (510, 580) for all websites in the configuration. The system of the present invention can be configured to work with either of these architectures. If each website has its own unique log file, then the log files are preferably entered into the system's 100 configuration, so that each website has its own area in the configuration. The system 100 will process the logs one at a time treating each website independently.

If the web server 500 is configured to log centrally, then the log file (510, 580) preferably contains some website identification marker in order for the system 100 to be able to sort and process the log file 510. As described previously, the website identification module 220 is designed to capture some parameter within the log file, in order to determine which hits go with which websites. This type of integration can automatically detect new websites as they are added to the web server 500 without modifying the configuration of the system 100.

Single Log vs. Multi-Log

The system and method of the present invention can be configured for systems that reside on one web server 500 or on multiple web servers 500. Multiple web servers 500 are often used for load-balancing, redundancy, and functional serving. Multiple web servers 500 will each have their own set of logs 510. The system and method of the present invention can automatically correlate the visitor centric data from multiple logs (510, 580), as described previously. By simply entering the multiple logs in the configuration, the system 100 will process the multiple logs.

E-Commerce vs. No-Commerce

As described previously, the system and method of the present invention can include e-commerce reporting functionality, and can be used in conjunction with shopping cart software. The e-commerce log files 580 are handled similarly to the multi-log architecture discussed above. The e-commerce logs 580 are simply treated as multiple logs. Additional entries will need to be made in the configuration.

For integration into e-commerce systems, the shopping cart software is preferably configured to create the preferred log file format described above.

Control Panel vs. Stand-Alone

Many larger hosting providers are creating centralized web-based control panels that contain links to all of the tools and systems available to the hosting clients. Hosting clients log into the control panel once and are provided with customized information and interaction, such as accessing their unique e-mail account, uploading files to their unique website, and viewing the reports created by the system of the present invention.

Stand-alone systems will have unique reporting directories for each website. Thus, accessing the reporting area is simple, as each reporting area will have a unique URL. Protecting report access can be accomplished through the web server 520 itself, and does not require integration with the system 100.

For control panel integrations, the system and method of the present invention is preferably sensitive to session controlling technology. As described previously, the session parser module 1420 has the ability to detect custom variables and control report delivery from a central location.

The various components of the present invention are preferably implemented on internet (e.g., web) servers, which may be or include, for instance, a work station running the Microsoft Windows™ NT™, Windows™ 2000, UNIX, LINUX, XENIX, IBM, AIX, Hewlett-Packard UX™, Novel™, Sun Micro Systems Solaris™, OS/2™, BeOS™, Mach, Apache Open Step™, or other operating system or platform. However, the various components of the present invention could also be implemented on a programmed general purpose computer, a special purpose computer, a programmed microprocessor or microcontroller and peripheral integrated circuit elements, an ASIC or other integrated circuit, a hardwired electronic or logic circuit such as a discrete element circuit, a programmable logic device such as a FPGA, PLD, PLA, or PAL, or the like. In general, any device on which a finite state machine capable of implementing the modules and control routines discussed above can be used to implement the present invention.

While the foregoing description includes many details and specificities, it is to be understood that these have been included for purposes of explanation only, and are not to be interpreted as limitations of the present invention. Many modifications to the embodiments described above can be made without departing from the spirit and scope of the invention, as is intended to be encompassed by the following claims and their legal equivalents.

What is claimed is:

1. A computer-implemented method, comprising:

receiving at a server from a client device a report request for a report related to web site traffic;

in response to the report request, sending from the server web site traffic data and application code to the client device, the application code comprising instructions that cause the client device to:

generate a report to display the web site traffic data;

time the display of the web site traffic data;

periodically request updated web site traffic data according to the time of the display;

update the report with the updated web site traffic data; and sending from the server to the client device the updated web site traffic data in response to the request for updated web site traffic data; and generating at the server the web site traffic data and the updated web site traffic data, wherein the web site traffic data and the updated web site traffic data each cause the client device to display a selectable graph depicting web site traffic parameter data;

wherein:

the application code further comprises instructions that cause the client device to generate, in response to a selection of a portion of the selectable graph corresponding to a point in time, a web site traffic parameter data request corresponding to a graphical depiction of the web site traffic parameter data corresponding to the selected point in time; and the web site traffic parameter data comprises visitor monitor data, the visitor monitor data including one or more of visitor data describing visitors to a web site, a number page views of the web site, a number of visits to the web site, and a time length of visits to the web site.

2. The computer-implemented method of claim 1, further comprising sending from the server the web site traffic parameter data to the client device in response to the web site traffic parameter data request.

3. The computer-implemented method of claim 2, further comprising:

correlating in the server commercial transaction data with the visitor monitor data; and generating return on investment reporting data from the correlation of the commercial transaction data with the visitor monitor data, the return on investment reporting data defining one or more of an amount spent per domain and an amount spent per visitor; and wherein the application code further comprises instructions that cause the client device to generate a return on investment report from the return on investment reporting data, the return on investment report displaying one or more of the amount spent per domain and the amount spent per visitor.

4. The computer-implemented method of claim 2, wherein the selectable graph depicts one or more of the number of visitors to the web site, the number page views of the web site, and the time length of visits to the web site.

5. The computer-implemented method of claim 2, wherein the application code further comprises instructions that cause the client device to generate a visitor monitor report that displays the visitor data describing visitors to the web site and one or more of the number page views of the web site, the number of visits to the web site, and the time length of visits to the web site.

6. The computer-implemented method of claim 5, wherein the application code further comprises instructions that cause the client device to:

request, in response to a selection of visitor data describing a visitor to the web site, visitor footprint data related to the visitor, the visitor footprint data including one or more of browser data, referral data, domain data and visitor path data; and generate a visitor footprint report that displays the visitor footprint data.

7. The computer-implemented method of claim 1, wherein the application code is JavaScript.

8. A system, comprising:

a data storage storing traffic information for a plurality of visitors to a web site;

one or more server computers in data communication with the data storage, the one or more server computers including application code and a reporting engine, wherein:

the application code comprises instructions that cause a client device to:

generate a report to display web site traffic data;

time the display of the web site traffic data;

periodically request updated web site traffic data according to the time of the display; and update the report with the updated web site traffic data; and the reporting engine is configured to generate the web site traffic data and the updated web site traffic data;

wherein:

the web site traffic data and the updated web site traffic data each cause the client device to display a selectable graph depicting web site traffic parameter data; and the application code further comprises instructions that cause the client device to generate, in response to a selection of a portion of the selectable graph corresponding to a point in time, a web site traffic parameter data request corresponding to a graphical depiction of the web site traffic parameter data corresponding to the selected point in time;

the web site traffic parameter data comprises visitor monitor data, the visitor monitor data including one or more of visitor data describing visitors to a web site, a number page views of the web site, a number of visits to the web site, and a time length of visits to the web site.

9. The system of claim 8, wherein the selectable graph depicts one or more of the number of visitors to a web site, the number page views of the web site, and the time length of visits to the web site.

10. The system of claim 9, wherein the application code further comprises instructions that cause the client device to generate a visitor monitor report that displays visitor data describing visitors to the web site and one or more of the number page views of the web site, the number of visits to the web site, and the time length of visits to the web site.

11. The system of claim 10, wherein the reporting engine is further configured to:

correlate in the server commercial transaction data with the visitor monitor data; and generate return on investment reporting data from the correlation of the commercial transaction data with the visitor monitor data, the return on investment reporting data defining one or more of an amount spent per domain and an amount spent per visitor; and wherein the application code further comprises instructions that cause the client device to generate a return on investment report from the return on investment reporting data, the return on investment report displaying one or more of the amount spent per domain and the amount spent per visitor.

12. The system of claim 9, wherein the application code further comprises instructions that cause the client device to:

request, in response to a selection of visitor data describing a visitor to the web site, visitor footprint data related to the visitor, the visitor footprint data including one or more of browser data, referral data, domain data and visitor path data; and generate a visitor footprint report that displays the visitor footprint data.

* * * * *